(12) United States Patent
Dapron et al.

(10) Patent No.: US 6,825,032 B2
(45) Date of Patent: Nov. 30, 2004

(54) HIGH CAPACITY ASSAY PLATFORMS

(75) Inventors: John Dapron, Oakville, MO (US); William Karl Kappel, Oakville, MO (US); Handong Li, San Jose, CA (US)

(73) Assignee: Sigma-Aldrich Co., Highland, IL (US)

( * ) Notice: Subject to any disclaimer, the term of this patent is extended or adjusted under 35 U.S.C. 154(b) by 0 days.

(21) Appl. No.: 09/854,638

(22) Filed: May 14, 2001

(65) Prior Publication Data

US 2003/0032013 A1 Feb. 13, 2003

(51) Int. Cl.[7] .................. C12M 1/34; G01N 33/544
(52) U.S. Cl. .................. 435/287.8; 435/174; 435/180; 435/181; 435/287.1; 435/287.2; 436/518; 436/529; 436/531; 436/532
(58) Field of Search ................. 435/174, 180, 435/181, 287.1, 287.2, 287.8; 436/518, 529, 531, 532

(56) References Cited

U.S. PATENT DOCUMENTS

| | | | |
|---|---|---|---|
| 4,309,453 A | | 1/1982 | Reiner et al. |
| 5,002,582 A | | 3/1991 | Guire et al. |
| 5,047,513 A | | 9/1991 | Dobeli et al. ............. 210/656 |
| 5,242,828 A | | 9/1993 | Bergström et al. |
| 5,336,762 A | | 8/1994 | Ranney |
| 5,512,329 A | | 4/1996 | Guire et al. |
| 5,624,711 A | * | 4/1997 | Sundberg et al. ........... 427/261 |
| 5,705,813 A | | 1/1998 | Apfell et al. |
| 5,792,331 A | * | 8/1998 | Srinivasan et al. ......... 204/451 |
| 5,858,653 A | | 1/1999 | Duran et al. |
| 5,900,481 A | | 5/1999 | Lough et al. |
| 6,124,137 A | | 9/2000 | Hutchens et al. |
| 6,133,436 A | | 10/2000 | Köster et al. |
| 6,225,061 B1 | | 5/2001 | Becker et al. |
| 6,288,390 B1 | * | 9/2001 | Siuzdak et al. ............ 250/288 |

FOREIGN PATENT DOCUMENTS

| | | | |
|---|---|---|---|
| WO | 92/03732 | 3/1992 | ......... G01N/33/543 |
| WO | WO 94/19694 A1 | 9/1994 | |

OTHER PUBLICATIONS

Kakabakos, S.E. et al., (1990) abstract of "Immunoadsorption of IgG Onto Second Antibody Covalently Attached to Amino–Dylark Beads for Radiommunoassays" *Clin Chem*, vol. 36, pp. 497–500.

Kakabakos, S.E. et al., "Colorimetric Determination of Amino Groups of CovaLink™ NH MicroWells™" http://www.nunclsdp.com/applications/bulletin/11.htm.

Pierce Chemical Company Application Notes, "Swell-Gel™" http://www.piercenet.com/WhatsNew/swell-glut.cfm?tmpl=swellglut.cfm.

Sigma–Aldrich, Inc. (Jun. 2000) Technical Bulletin—Sigmascreen™ (Nickel Chelate Affinity Matrix, High Capacity).

Qiagen, "Ni–NTA HisSorb™ Strips and Plates" http://www.qiagen.com/catalog/chapter_03/chap3d2.asp.

Sigma Life Science Catalog (mailed Jun. 11, 2000), "Ni–CAM HC Multiwell Plate".

Hassell, Torn et al., High Throughput Purification and Characterization of Poly–His Proteins by MALDI–TOF Mass Spectrometry; 48th Conference on Mass Spectrometry and Allied Topics Jun. 11–15, 2000, Long Beach, California.

Barbacci, Layle K. and Zobrist, Jodi M., On Target Affinity Purification for MALDI–MS Analysis; 49th Conference on Mass Spectrometry and Allied Topics, May 27–31, 2001, Chicago, Illinois.

Orbit News, Dec. 2000, http://www.messebasel.ch/miptec/index.htm.

Press Release, Nov. 20, 2000, Sigma–Aldrich Scientist Receives PolyPops Award for Outstanding Contribution to Microtiter Plate Product Development.

Working With Genes, Analytical Report, Mar. 2001.

Rasmussen, et al., "Convalent Immobilization of DNA onto Polystyrene Microwells: The Molecules Are Only Bound at the 5' End," *Anal. Biochem.* vol. 198, pp. 138–142 (1991).

Rasmussen "Covalent Immobilization of Biomolecules Onto Polystyrene MicroWells for Use in Biospecific Assays," *Ann. Biol. Clin.*, vol. 48, pp. 647–650 (1990).

Nakamura, R., et al., "A Plasma–Polymerized Film for Surface Plasmon Resonance Immunosensing," Anal. Chem., Nov. 15, 1997, pp. 4649–4652, vol. 69(22).

International Search Report for PCT/US02/13422 dated Jul. 2, 2003, 3 pages.

Supplementary European Search Report for EP 02 72 9040 dated Jun. 24, 2004, 4 pages.

* cited by examiner

*Primary Examiner*—Padmashri Ponnaluri
*Assistant Examiner*—My-Chau T Tran
(74) *Attorney, Agent, or Firm*—Senniger Powers

(57) ABSTRACT

A high capacity assay platform capable of binding target molecules includes a substrate and a polymer matrix attached to the substrate. The polymer matrix comprises a plurality of polymer molecules where at least some of the polymer molecules are covalently attached directly to the substrate and at least some of which molecules are crosslinked to other polymer molecules. Some of the polymer molecules have at least one binding ligand covalently attached thereto, and the density of the polymer matrix on the substrate is at least 2 $\mu g/cm^2$.

60 Claims, 1 Drawing Sheet

HIGH CAPACITY ASSAY PLATFORMS

FIELD OF THE INVENTION

This invention relates to assay platforms for isolating, harvesting, detecting and/or quantitating target molecules, e.g., polypeptides, nucleotides or biomolecules, in or from a sample. More particularly, the invention relates to multiwell assay plates and other assay platforms carrying a polymer matrix having a high density of binding ligands distributed therein.

BACKGROUND OF THE INVENTION

A variety of approaches and techniques have been proposed and employed to provide assay platforms for high throughput, multi-sample screening. Multiwell plates have been treated, for example, to detect binding interactions. These assay plates have a relatively low density of functional binding ligands. Consequently, the binding or capture capacities of these assay plates are at sub-microgram levels and application potential is generally restricted to detection analysis.

Solid supports made of polystyrene, polypropylene and glass, such as multiwell plates, glass slides, solid chromatography beads, sheets and tubes, are not suitable for the binding and isolation of multi-microgram amounts of high molecular weight target molecules per square centimeter including proteins, nucleic acids and polypeptides. To date no one has been able to develop on a solid support a high density, high capacity, three dimensional structure that has the appropriate architecture for binding large quantities of proteins and other molecular components. Attempts to covalently attach synthetic and natural polymers to supports have not been successful in significantly increasing the binding capacity of the supports over that obtained with passive adsorption.

The challenge of isolating and identifying total protein expressed in an organism in the rapidly growing field of proteomics requires advances in technologies such as sample preparation, purification and characterization. Current methods for isolation of proteins and other molecules require a considerable amount of effort, which generally includes employing time consuming chromatography or electrophoretic techniques. The current surface-derivatized multiwell plate systems lack sufficient surface area, porosity, and ligand density for the fast isolation of the microgram quantities needed for the characterization of proteins, nucleic acids and other biomolecules.

Attempts by others to develop a method of rapidly and specifically isolating multi-microgram amounts of proteins and other molecules per square centimeter of surface from crude cellular extracts, allowing isolation and characterization of protein, have been unsuccessful. Previous failed attempts included covalently attaching a large amount and variety of natural and synthetic molecules to flat surfaces through standard organic or photochemical means.

SUMMARY OF THE INVENTION

The present invention provides an assay platform comprising a substrate and a polymer matrix attached to the substrate, wherein the polymer matrix is capable of binding target molecules, wherein the polymer matrix comprises a plurality of polymer molecules, wherein at least some of the polymer molecules are covalently attached directly to the substrate, wherein at least some of the polymer molecules are crosslinked to other polymer molecules, wherein at least some of the polymer molecules have at least one binding ligand covalently attached thereto, and wherein the density of the polymer matrix on the substrate is at least 2 $\mu g/cm^2$.

The present invention also provides a method of preparing an assay platform comprising a substrate and a polymer matrix attached to the substrate, wherein the polymer matrix is capable of binding target molecules comprising:

contacting the substrate with a polymer composition comprising a plurality of polymer molecules having repeating units, wherein at least some of the polymer molecules have at least one reactive group covalently attached thereto, wherein at least some of the polymer molecules have at least one binding ligand covalently attached thereto, wherein the polymer molecules have an average molecular weight of at least 100 kDa, and wherein at least 25% of the polymer molecules have at least one reactive group and at least one binding ligand covalently attached thereto; and activating the reactive groups to covalently bind at least some of the polymer molecules directly to the substrate and to induce cross-linking between polymer molecules to form a polymer matrix attached to the substrate.

The present invention also provides a polymer composition comprising a plurality of polymer molecules having repeating units, wherein at least some of the polymer molecules have at least one reactive group covalently attached thereto, wherein at least some of the polymer molecules have at least one binding ligand covalently attached thereto, wherein the polymer molecules have an average molecular weight of at least 100 kDa, and wherein at least 25% of polymer molecules have at least one reactive group and at least one binding ligand covalently attached thereto.

DETAILED DESCRIPTION OF THE INVENTION

Figure 1:
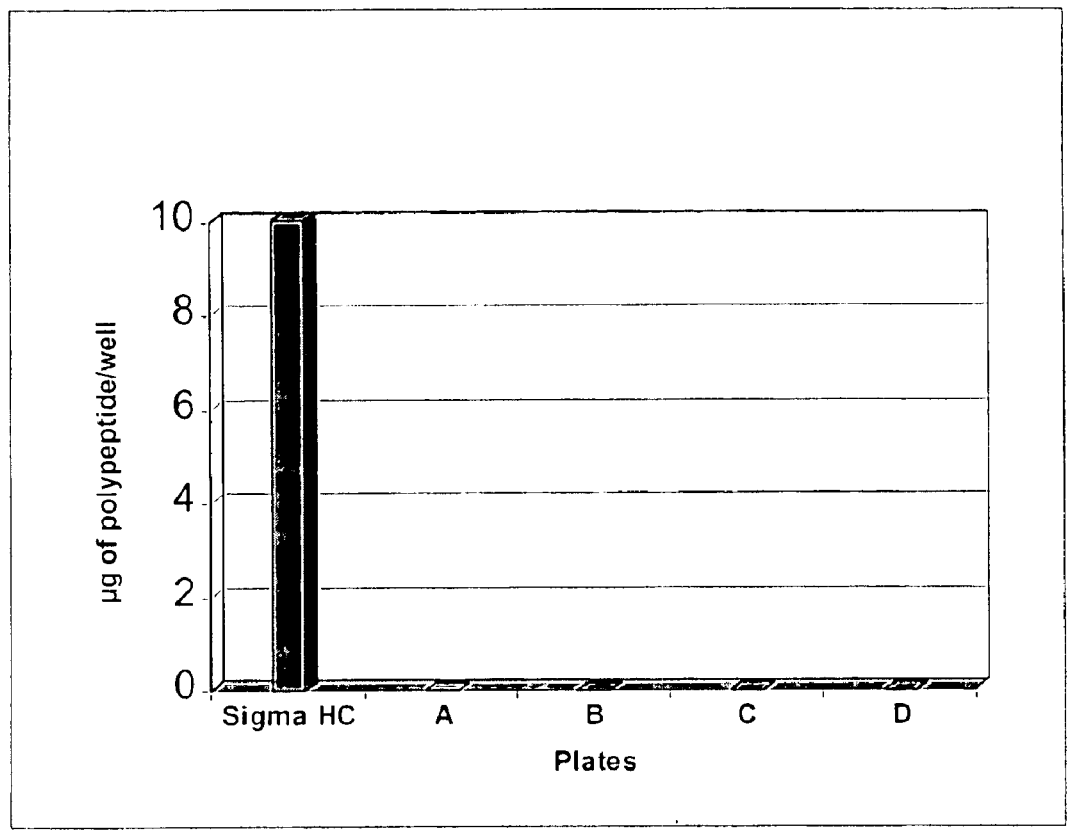
FIG. 1 compares the polypeptide binding capacity of an assay platform according to the invention to the polypeptide binding capacity of three commercial plates.

The high capacity assay platform of the invention overcomes the binding capacity limitations associated with currently available platforms. As will be described below, the present invention enables the rapid and specific isolation of multi-microgram amounts of proteins and other target molecules, from even crude cellular extracts. The invention enables one of skill in the art to characterize the isolated target molecule by standard biochemical methods, such as SDS PAGE, mass spectrometry or Western blotting. A surprising and advantageous aspect of this invention is that a three dimensional polymer matrix comprised of high density functionalized ligands and a controllable pore size can be bound to a solid surface and used to isolate proteins and biomolecules in a wide range of molecular weights. The porosity controllable three dimensional matrix can be tailored to meet the specific demands of the target.

The assay platforms of the invention may be prepared and used for isolating, detecting and/or quantitating a variety of target molecules, for example, peptides, polypeptides, large proteins, antibodies, glycoproteins, DNA, RNA and polysaccharides. As used herein, a polypeptide is any peptide having at least two amino acids. A polypeptide may be a natural polypeptide or a synthetic polypeptide, e.g., recombinant or combinations thereof. The assay platforms of the invention may also be prepared and used to bind small organic molecules, drugs, small proteins, peptides, chemically modified polypeptides, oligonucleotides or small polymers and compounds with smaller molecular weights. Selection of an appropriate pore size allows one of skill in the art to advantageously develop a format that offers selectivity and high binding capacity.

The assay platforms of this invention comprise a substrate and a polymer matrix covalently attached to the substrate.

The substrate may be a material having a rigid or semi-rigid surface. The surface may be flat, curved and/or both. Additionally, the assay platform of the invention may be provided in any desired form, size and shape. Examples of suitable substrates include plastic, glass, polystyrene beads, magnetic particles, other microparticles, polystyrene multi-well plates, polypropylene multiwell plates, polycarbonate multiwell plates, plasma-treated polystyrene surfaces, and Matrix assisted laser desorption ionization (MALDI) plates. MALDI mass spectrometry is used for molecular weight determination. The method is critical in the area of proteomics and is used to analyze proteolytic fragments or whole proteins obtained from crude or purified biological samples. Samples are analyzed by MALDI mass spectrometry by placing the samples at specific locations or spots on a MALDI plate. A MALDI plate is the solid support used to deliver the sample to the mass spectrometer and is also know as a MALDI target or MALDI probe capable of handling irradiation by a laser during the analysis. Preferred assay platforms are multiwell plates, e.g., polystyrene or polypropylene multiwell plates containing 48, 96, 384 or 1536 individual wells.

As used herein, plastic is understood to be any of a group of synthetic or natural organic materials that may be shaped when soft and then hardened, including many types of resins, resinoids, polymers, cellulose derivatives, casein materials, and proteins. Plastic materials, often called resins, are made up of many repeating groups of atoms or molecules linked in long chains (called polymers) that combine elements such as oxygen, hydrogen, nitrogen, carbon, silicon, fluorine, and sulfur. Both the lengths of the chains and the mechanisms that bond the links of the chains are related directly to the mechanical and physical properties of the materials. Characteristics of plastics materials can be changed by mixing or combining different types of polymers and by adding nonplastics materials. Particulate fillers such as wood, flour, silica, sand, ceramic, carbon powder, tiny glass balls, and powdered metal are added to increase modulus and electrical conductivity, to improve resistance to heat or ultraviolet light and to reduce cost. Plasticizers are added to decrease modulus and increase flexibility. Other additives may be used to increase resistance to ultraviolet light and heat or to prevent oxidation.

As used herein, glass is understood to be a brittle, noncrystalline, usually transparent or translucent material that is generally formed by the fusion of dissolved silica and silicates with soda and lime. Glass is further understood to be any of a large class of materials with highly variable mechanical and optical properties that solidify from the molten state without crystallization, that are typically based on silicon dioxide, boric oxide, aluminium oxide, or phosphorus pentoxide, that are generally transparent or translucent, and that are regarded physically as supercooled liquids rather than true solids.

The polymer matrix attached to the substrate comprises a plurality of polymer molecules wherein at least some of the polymer molecules have at least one binding ligand covalently attached thereto. As used herein, a binding ligand shall be understood to mean a moiety that binds to a target molecule by formation of either a covalent or noncovalent bond between the target molecule and the binding ligand. A covalent bond is a strong chemical bond between the binding ligand and the target molecule by a sharing of electrons. A noncovalent bond is a weak chemical bond arising from nonspecific attractive forces of atoms oriented close together. The bonding between the binding ligand and target molecule may be ionic or electrostatic, hydrogen bonding, or hydrophobic/hydrophilic interactions or non-covalent.

The density of the polymer matrix on the substrate may be controlled by, inter alia, selection and amounts of the particular polymer and reactive groups employed. The molecular weight of the polymer, the number and type of reactive group and the number and molecular weight of the binding ligands may be selected and adjusted, as detailed further below and as illustrated in the Examples. The polymer matrix may be attached to all of the substrate or to only a part of the substrate. For example, only the wells or a portion of the wells of multiwell plates may be provided with the polymer matrix. Examples of other substrate include, beads completely covered by the polymer matrix.

Generally, the density of the polymer matrix on the substrate (total mass of polymer, including covalently attached spacers and reactive groups) is at least 2 $\mu g/cm^2$. In preferred embodiments, the polymer matrix has a density of 4 $\mu g/cm^2$ to 30 $\mu g/cm^2$, e.g., 6 $\mu g/cm^2$ to 15 $\mu g/cm^2$.

Examples of suitable binding ligands which may be provided in the polymer matrix include, but are not limited to: metal chelates, anion exchangers, cation exchangers, affinity ligands, hydrophobic binding ligands, chromatography ligands, chemically reactive ligands, covalent attachment sites, homobifunctional organic nucleophiles, polypeptides, a polynucleotide, an oligo dT, or a multivalent cation, wherein the multivalent cation is selected from the group consisting of copper, zinc, cobalt, gallium, iron and nickel. Illustrative binding ligands include agonists and antagonists for cell membrane receptors, toxins and venoms, viral epitopes, hormones, amino acids, peptides, polypeptides, enzymes, enzyme substrates, cofactors, drugs, lectins, dyes, nucleotides, phenylboronates, sugars, carbohydrates, biotin, avidin, streptavidin, oligonucleotides, nucleic acids, oligosaccharides, proteins, chelates, enzyme inhibitors, and antibodies. The protein affinity binding group may be streptavidin or avidin and the chelator might be tetradentate nitriloacetic acid (NTA).

A metal chelator may be formed by the addition of a metal or a metal oxide to a chelating composition. Various metal chelators are currently available and may be used as a binding ligand of the invention. U.S. patent application Ser. No. 09/558,001, filed Apr. 24, 2000 and entitled "Metal Chelating Compositions," discloses various suitable metal chelates and how they are produced, and is herein incorporated by reference. Additional metal chelators are known to those skilled in the art and include iminodiacetic acid, nitriloacetic acid or an analog thereof and diethylenetriamine pentacetic anhydride. In the most preferred embodiment of this invention the metal chelate is nickel, gallium, or iron.

An ion-exchanger may be a basic or acidic molecule covalently bound to the polymer matrix that can interact or bind to molecules in solution, including macromolecules such as an enzyme, via charge interaction. The ion-exchange ligand may contain a nitrogen group, a carboxyl group, a phosphate group, or a sulfonic acid group. Examples of ion-exchanger binding ligands include diethylaminoethyl (DEAE), diethyl[2-hydroxypropyl]aminoethyl (QAE), carboxymethyl (CM), and sulfopropyl (SP), and phosphoryl. See, Sigma Chemical Biochemicals and Reagents 2000–2001 catalog, pages 1888–1899.

A hydrophobic binding ligand is a molecule covalently bound to the polymer matrix possessing hydrophobic properties that can interact or bind to molecules in solution, including macromolecules such as an enzyme, via hydrophobic interaction. Examples of hydrophobic ligands are phenyl, hexyl, octly, and C18 groups. See, Sigma Chemical Biochemicals and Reagents 2000–2001 catalog, pages 1936–1940.

A binding ligand can be a polypeptide, for example an antibody or proteins involved in protein-protein interaction. Alternatively, the binding ligand can be any of the examples stated above which are capable of binding any target molecule including nickel, a polypeptide target molecule, a polynucleotide, or other biomolecules. A binding ligand can be an amino acid, e.g., lysine, or a polypeptide having a molecular weight of 100 kDa or more, e.g., an IgG.

A binding ligand can be an oligonucleotide. The oligonucleotide binding ligand is capable of binding mRNA, cDNA or DNA and in turn may be used to perform RT-PCR. An illustrative binding ligand is oligo dT.

The density of binding ligands in the polymer matrix may vary and may be selected or adjusted by changing the number and/or molecular weight of the ligands covalently attached to the polymer molecules of the matrix. Generally the density of binding ligands in the polymer matrix may be a least 1 nanomole/cm$^2$. In some embodiments of the invention the density of the binding ligands may be 1.2 nanomoles/cm$^2$ to 185 nanomoles/cm$^2$. In another embodiment of the invention the density of the binding ligands may be 1.5 nanomoles/cm$^2$ to 90 nanomoles/cm$^2$, e.g., 1.8 nanomoles/cm$^2$ to 15 nanomoles/cm$^2$.

Through the selection and combination of various polymers and binding ligands, and by providing and controlling the cross-linking of polymer molecules in the matrix, the assay platforms of the invention enable the high capacity capture of target molecules in ranges not heretofore achieved.

The polymer matrix of the assay platforms of the invention is capable of binding target molecules having a molecular weight of less than 3.5 kDa in an amount of at least 1 nanomole/cm$^2$.

The polymer matrix may be constructed to be capable of binding target molecules having a molecular weight of 3.5 kDa to 500 kDa in an amount of 0.5 μg/cm$^2$ to 20 μg/cm$^2$, a molecular weight of 10 kDa to 500 kDa in an amount of 1 μg/cm$^2$ to 20 μg/cm$^2$, a molecular weight of 10 kDa to 350 kDa in an amount of 2 μg/cm$^2$ to 20 μg/cm$^2$, a molecular weight of 10 kDa to 350 kDa in an amount of 3 μg/cm$^2$ to 15 μg/cm$^2$. In some embodiments, the polymer matrix is capable of binding target molecules with a molecular weight of 10 kDa to 350 kDa in an amount of 4 μg/cm$^2$ to 10 μg/cm$^2$. In certain embodiments the polymer matrix is capable of binding polypeptide target molecules having a molecular weight up to 350 kDa in an amount of at least 2 μg/cm$^2$ of polymer matrix.

The assay platforms of the invention may be prepared by contacting a substrate with a polymer composition comprising a plurality of polymer molecules having repeating units, wherein at least some of the polymer molecules have at least one reactive group covalently attached thereto, wherein at least some of the polymer molecules have at least one binding ligand covalently attached thereto, wherein the polymer molecules have an average molecular weight of at least 100 kDa, and wherein at least 25% of the polymer molecules have at least one reactive group and at least one binding ligand covalently attached thereto. The reactive groups are activated to covalently bind at least some of the polymer molecules directly to the substrate and to induce cross-linking between polymer molecules to form a polymer matrix attached to the substrate.

The polymer molecules have repeating units that may be the same or different and the polymer molecules may be linear or branched. For example, if the polymer molecules of the composition are proteins or polypeptides, the repeating units would be amino acids. If the polymer molecules of the composition are carbohydrates, the repeating units could be glycosyl groups. Prefered polymers are non-polynucleotides.

The polymers may include several distinct polymer types, as prepared by terminal or side chain grafting. Some examples of distinct polymer types include, but are not limited to, cellulose-based products such as hydroxyethyl cellulose, hydroxypropyl cellulose, carboxymethyl cellulose, cellulose acetate and cellulose butyrate, acrylics such as those polymerized from hydroxyethyl acrylate, hydroxyethyl methacrylate, glyceryl acrylate, glyceryl methacrylate, acrylic acid, methacrylic acid, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide; polyurethanes, polylactic acids, linear polysaccharides such as amylose, dextran, chitosan, heparin and hyaluronic acid, and branched polysaccharides such as amylopectin, hyaluronic acid and hemi-celluloses. Blends of two or more different polymer molecules can be used. For example, in one embodiment the polymer molecules are a mixture of dextran and heparin. In another embodiment dextran is mixed with poly Lys-Gly (1 lysine per 20 glycine).

The polymers of the composition may be either natural or synthetic polymers and modified natural or modified synthetic polymers. The polymers may also be dextran polymers. Natural polymers are branched or linear polymers produced in a biological system. Examples of natural polymers include but are not limited to oligosaccharides, polysaccharides, peptides, proteins, glycogen, dextran, heparin, amylopectin, amylose, pectin, pectic polysaccharides, starch, DNA, RNA, and cellulose. A particular modified natural polymer that may be used is a dextran-lysine derivative produced by covalently inserting lysine into variable linear positions along the dextran molecule using periodate oxidation and reductive amination or other methods known to those of skill in the art.

Synthetic polymers are branched or linear polymers that are manmade. Examples of synthetic polymers include plastics, elastomers, and adhesives, oligomers, homopolymers and copolymers produced as a result of addition, condensation or catalyst driven polymerization reactions, i.e., condensation polymerization.

Modified natural polymers are natural polymers that have been chemically modified. Chemical modifications can be done by, but are not limited to, oxidation, or the covalent attachment of photo-reactive groups, affinity ligands, ion exchange ligands, hydrophobic ligands, other natural or synthetic polymers, and spacer molecules.

Modified synthetic polymers are synthetic polymers that have been chemically modified. Chemical modifications can be done by, but are not limited to, oxidation, or the covalent attachment of photo-reactive groups, affinity ligands, ion exchange ligands, hydrophobic ligands, or other natural or synthetic ligands.

The polymer molecules have an average molecular weight (total molecular weight of polymer, including covalently attached functional groups) of at least 100 kDa, e.g., 300 kDa to 6,000 kDa. In some embodiments the polymer molecules have an average molecular weight of 400 kDa to 3,000 kDa. In another embodiment the polymer molecules have an average molecular weight of 500 kDa to 2,000 kDa. For purposes of this invention the average molecular weight is the weight average molar mass (Mw) value of a polymer as measured by gel filtration chromatography using multi-angle light scattering and refractive index detection. The average Mw of the polymer distribution of all chain lengths present is based upon the selection of the peak as measured by the refractive index, starting and ending peak selection criteria of a refractive index value that is three times the refractive index baseline. As shown by example a preferred polymer may have an average Mw of 1,117 kDa with a molecular weight range from 112 kDa to 19,220 kDa.

At least some of the polymer molecules of the composition contacted with the substrate have at least one binding ligand covalently attached thereto and at least some of the polymer molecules of the composition have at least one reactive group covalently attached thereto. As used herein a reactive group is a chemical moiety that is capable of covalently bonding to the substrate. In addition, the reactive group may also be capable of covalently bonding to polymer molecules in the composition. This interaction of the reactive group between polymer molecule results in a cross-linking which forms the three-dimensional matrix. The reactive group reacts either thermochemically or photo-chemically (polymers that contain a photo-reactive group are referred to as being photolabeled).

Reactive groups include, but are not limited to, reactive groups used in the preparation of chromatography media which include; epoxides, oxiranes, N-hydroxysuccinimide, aldehydes, hydrazines, maleimides, mercaptans, amino groups, alkylhalides, isothiocyanates, carbodiimides, diazo compounds, tresyl chloride, tosyl chloride, and trichloro-S-triazine. For examples see, Methods in Enzymology Volume 34, Affinity Techniques, Enzyme Purification Part B, edited by William B. Jakoby and Meir Wilchek, Academic Press, New York, 1974, pp 1–809, hereby incorporated by reference.

Preferred reactive groups are α, β unsaturated ketone photo-reactive groups. For purposes of this invention a photo-reactive group is a molecule or moiety that forms a highly reactive species upon exposure to light. Examples of photo-reactive groups include aryl azides, diazarenes, beta-carbonyldiazo, and benzophenones. The reactive species are nitrenes, carbenes, and radicals. These reactive species are generally capable of covalent bond formation. Preferred photo-reactive groups are photoactivatable, unsaturated ketones such as acetophenones, benzophenones and derivatives thereof. For examples see, Laboratory Techniques in Biochemistry and Molecular Biology: Photogenerated Reagents in Biochemistry and Molecular Biology, Hagan Bayley, Elsevier, N.Y., 1983, pp 1–187, hereby incorporated by reference.

The examples, which follow, depict a photo-reactive group that when contacted with light becomes activated and is capable of covalently attaching to the surface of a solid substrate. For example the photo-reactive groups may be activated by exposure to UV light from about 3 Joules/cm$^2$ to about 6 Joules/cm$^2$ depending on the intensity of light and duration of exposure time. The exposure times may range from as low as 0.5 sec/cm$^2$ to approximately 32 min/cm$^2$ depending on the intensity of the light source. In a preferred embodiment, the photo-reactive groups are activated by exposure to light for 0.5 sec/cm$^2$ to 5.0 sec/cm$^2$ at about 1,000 mWatts/cm$^2$ to about 5,000 mWatts/cm$^2$, or from about 1,000 mWatts/cm$^2$ to about 3,000 mWatts/cm$^2$, e.g., 1,500 mWatts/cm$^2$ to about 2,500 mWatts/cm$^2$.

There are many UV irradiation systems capable of delivering the total energy (dosage measured in Joules) required to bond the photo-activated polymer to a hydrocarbon rich substrate. Irradiation may be provided by a mercury lamp which has a distinct and known wavelength pattern of irradiation. The intensity of irradiation requires Joules to fall in the range of 3–6 Joules/cm$^2$. Joule measurements encompass the time factor (1 Joule=watt×second). In an embodiment of this invention the irradiation is provided by an electrodeless mercury lamp powered by microwave radiation. One six inch, 500 watt/in. lamp has a rated power output of 2,500 mWatts/cm$^2$ measured in the UVA range at about 2 inches distance of lamp to substrate. The lamp can be successfully run at 80% power or approximately 2,000 mWatts/cm$^2$. Sample plates prepared using a standard low intensity UV irradiation box having an intensity of irradiation (UVA/UVB, approximately 250 to 350 nm) measured at approximately 9.0 mWatts/cm$^2$ and requiring greater than 10 Joules/cm$^2$ (10,000 mJoules) total energy to provide good bonding. This requires an incubation time of the sample plates in the irradiation box of greater than 20 minutes. Plates processed using an electrodeless mercury lamp (2,000 mWatts/cm$^2$) irradiation system requires only 1.75 sec/cm$^2$ for a total energy dosage of 3.5 Joules/cm$^2$. The higher intensity irradiation more efficiently activates the photo-active groups and consequently a lower overall energy dosage is required.

Binding ligands and/or reactive groups may be covalently attached to the polymer molecules via a spacer. For purposes of this invention a spacer is a molecule or combination of covalently bonded molecules that connect the polymer molecule and either one or more of a binding ligand or reactive group. The spacer can be the same or different for any polymer, polymer composition or polymer matrix. Those of skill in the art will know that many types of spacers are available and the selection and use is dependent upon the intended application of the polymer matrix, e.g., a lysine molecule or a aminocaproic acid molecule.

The spacer can be covalently attached to the photo-reactive group by a number of different chemistries including amide formation. For example, the use of the hydrocarbon spacer dramatically enhances polymer matrix stability performance. A photo-reactive group with a spacer may be coupled to a portion of a primary amine of the preferred polymer dextran by an amide bond at a controlled ratio relative to total monomer, glucose. For examples of spacers see the review by Jakoby and Wilchek, hereby incorporated by reference. Id at 1–809.

Examples of photo-reactive groups with a spacer include, but are not limited to, benzobenzoic aminocaproic, N-Succinimidyl-N'-(4-azido-salicyl)-6-aminocaproate, N-Succinimidyl-(4-azido-2-nitrophenyl)-aminobutyrate, and N-Succinimidyl-(4-azido-2-nitrophenyl)-6-aminocaproate. These photo-reactive groups with spacers may be reacted with a polymer to produce a spacer that now includes the lysine as well as the original spacer attached to the photo-reactive group. The spacer can also be manufactured by incorporating multiple molecules such as lysine and aminocaproic acid prior to attaching the photo-reactive group containing or not containing an additional spacer. An example of a reactive group covalently attached to a polymer molecule is a spacer comprising a moiety or residue of lysine bound to one or more chemical entities of the reactive group, by the loss of a reactive hydrogen from the amino group.

The functioning of the polymer matrix is dependent on the spacing and number of binding ligands and reactive groups covalently attached to the polymer molecules in the composition. This aspect of the invention is illustrated in the examples.

As illustrated, the density of primary amines contributed by the lysine spacers represents the density of desired binding ligand and reactive group. Modified polymers containing primary amines or other moieties such as spacers in a range of one moiety per every 1 to 100 polymer repeating units may be made by procedures known in the art. Modification of these moieties to selectively incorporate the desired amount of reactive groups is also known. For example, the density of the primary amines contributed by the lysine spacers is on average 1 for every 12 repeating glucose units of the dextran polymer. This density is very high relative to the desired incorporation of photo-reactive groups, e.g., less than one photo-reactive group per 200 repeating monomers. The concentration of primary amines in solution during polymer manufacture might be 4.5 $\mu$moles/mL, whereas the desired incorporation of photo-reactive groups would represent 0.09 $\mu$moles/mL. Therefore, in this instance, there would be a 50-fold excess of primary amine to the required photo-reactive group incorporation via a reactive ester. At this concentration of amine, employing the methodologies described in the examples, the addition of photo-reactive group via a reactive ester at the desired level of incorporation results in greater than 90% efficiency of incorporation. By varying the amount of photo-reactive group containing a reactive ester any incorporation level less than 1 reactive group per 200 monomers can be consistently achieved. The method required to efficiently convert each of the remaining spacer moieties or amines to binding ligand attachment points is known in the art. A several fold excess of an amine reactive, e.g., reactive ester, derivatization reagent is used for the attachment of the binding ligand, either directly in one step or through multiple steps. In some cases, the derivatization reagent will present an additional reactive group which, depending on its reactivity, will dictate the stoichiometry for subsequent binding ligand attachment. When lower ligand density is desired the initial amine reactive derivatization reagent will be lowered accordingly. In some instances free amines remaining after selective modifications will generally be derivatized by acetylation.

When the polymer molecules have reactive groups covalently attached, the number of reactive groups is preferably less than 1 reactive group per 200 repeating units. In another embodiment the polymer molecules have less than 1 reactive group per 600 repeating units.

When the polymer molecules have binding ligands covalently attached the ligands have from 1 binding ligand per 1 repeating unit to 1 binding ligand per 100 repeating units. In another embodiment the binding ligands covalently attached thereto have from 1 binding ligand per 1 repeating unit to 1 binding ligand per 20 repeating units.

In a preferred embodiment of the invention the polymer molecules contacted with the substrate have at least one binding ligand covalently attached thereto and at least some of the polymer molecules have no reactive group covalently attached thereto. The percentage of polymer molecules having both reactive groups and binding ligands covalently attached may be 25% to 80%. In another embodiment the percentage of both reactive groups and binding ligands attached may be from 40% to 75%. In yet another embodiment the percentage of both reactive groups and binding ligands attached may be from 50% to 60%. In the preferred embodiment the percentage of polymer molecules having both reactive groups and binding ligands covalently attached thereto may be approximately 50%. The use of a mixture of polymer molecules, with and without reactive groups, enhances the highly functional formation of a three dimensional polymer matrix.

The first step in coating a surface of a substrate is contacting the polymer composition with the substrate surface to be coated. The method used to contact the polymer composition with the surface depends on the dimensions and shape of the surface to be coated. The surfaces can be made, for example, from material selected from the group consisting of polystyrene, polypropylene, polyesters, polyethylene, silica, glass, latex, plastic, gold, iron oxide, polyacrylamide, nucleic acid, lipids, liposomes, synthetic polymers, proteins, polyaminoacids, albumins, antibodies, enzyme, streptavidin, peptides, hormones, and polysaccharides. The surface can be derivatized prior to coating. Pre-derivatization can be done by any method known by one of skill in the art, including silanization of silica and glass and plasma treatment of polystyrene or polypropylene to incorporate amines, carboxyl groups, alcohols, aldehydes and other reactive groups or by chemical modification of the surface to change its chemical composition.

If necessary, the surface of the substrate may be chemically modified to facilitate covalent bonding with the reactive groups carried on the polymer molecules. Such modifications include treating the substrate surface with a hydrocarbon, or plasma-treating the surface. An illustrative example of a chemical modification is the silanization of glass. In a preferred embodiment a MALDI plate is dipped into a 1 mg/mL solution of parafilm dissolved in chloroform and dried.

When coating a multiwell plate, tube or a surface or a portion thereof, larger than 0.1 mm square the polymer composition may be contacted with the surface by pouring, mirco-pipeting, or transferring the polymer composition onto the portions of the plate, i.e., wells to be coated. In the alternative, the portion of the plate, tube or a surface larger than 2 mm square to be coated may also be coated by dipping the portion of the surface into a solution of the polymer composition so as to place the surface in contact with the polymer composition. In the case of smaller surfaces, such as beads or chips, the surfaces can be dispersed into a container possessing the polymer composition wherein the smaller surfaces are placed in direct contact with the polymer composition. In addition, once the beads or chips are placed into a container having the polymer composition, the polymer composition containing the surfaces to be coated can be stirred, agitated, or mixed to assure contact of the surfaces to be coated with the polymer composition.

The amount of polymer that attaches to the solid surface may be adjusted or controlled by varying the polymer composition concentration and volume added to the substrate. Once the polymer composition is placed in contact with the surface, the polymer composition may be dried on the substrate prior to activating the reactive groups, for example, evaporated to dryness by incubation in the dark at 20–50° Celsius with air flow. The polymer composition can also be evaporated using lyophilization or by any other drying means, including air drying, to remove the solvent. A variety of drying methods may be used provided that there is no premature activation of the reactive groups in response to the drying step. The substrate is considered sufficiently dry when no moisture is detectable visibly. During the drying the polymer molecules of the polymer composition orient themselves so as to bind with the substrate surface or interact with each other to promote inter and intra-crosslinking with other polymers of the polymer composition.

The dried coated solid surface is then treated to induce the reactive groups to covalently bond to the substrate. In the case of the photo-reactive groups they may be activated by irradiation. Activation is the application of an external stimulus that causes reactive groups to bond to the substrate. Specifically, a covalent bond is formed between the substrate and the reactive group, e.g., carbon-carbon bond formation.

In an embodiment activation may be done with a UVA/UVB light irradiating at 9.0 mWatts/cm$^2$ for approximately 30 minutes to a total energy of approximately 15,000 mjoules/cm$^2$. In a preferred embodiment activation may be done by exposure to UVA/UVB light irradiating at 2,000 mWatts/cm$^2$ to a total energy of from about 3 Joules/cm$^2$ to about 4 Joules/cm$^2$. The amount of incubation time and the total energy used may vary according to the photo-reactive group bound to the polymer. In the most preferred embodiment, activation may be done by photoirradiation using a Fusion UV Conveyor System using a mercury electrodeless lamp irradiating at 2,000 mWatts/cm$^2$ with the conveyer belt set at 8 feet/minute with the lamp power at 400 watts/in. A radiometer, IL290 Light Bug, is run through the conveyer belt to verify the desired energy in the range of 3,000–4,000 mjoules/cm$^2$. The multiwell plates are photoir-radiated at about 800 plates per hour, or about 1 plate per 4 to 5 seconds.

The concentration of the polymer composition of the present invention can be adjusted by changing the amount of total polymer per milliliter of solvent. In the case where a higher concentration of polymer composition or polymer matrix per square cm would be advantageous, less solvent can be used to solvate the polymer molecules of the composition. In the case where a lower concentration of polymer composition or polymer matrix per square cm would be advantageous, more solvent can be used to solvate the polymer molecules of the composition. In other words, adjusting the concentration of the polymer composition between 0.02 and 1.0 mg/mL solvent and coating a solid surface such as a multiwell plate would produce a surface having a selectable range of total bound polymer matrix. The polymer composition can be completely soluble or contain suspended insoluble polymer. The solvents that may be used to make the composition of the present invention include water, alcohols, ketones and mixtures of any or all of these. The solvents must be compatible with substrate being used. Since the polymers of the composition may crosslink between each other, it is possible that a fluid-like solution of the composition may change into a gel. In the alternative, the solution may be produced in the form of a slurry. Examples of solvents that may be used in the composition include water, alcohols, ketones and mixtures of any or all of these.

Non-bound polymers may be removed by incubating in a suitable solution to dissolve and remove unbound polymer. For example, multiwell plates may be incubated with MOPS buffer overnight at 25° C., washed with MOPS buffer and distilled water three times each, washed with hibitane solution, air dried, packaged and stored below ambient temperature (2–8° C.). The remaining polymers form the polymer matrix.

Of the polymers that remain, at least some of the polymer molecules of the composition have at least one reactive group covalently attached thereto. Some of the polymer molecules bind directly to the substrate through the reactive group, whereas some reactive groups covalently bind between polymer molecules. The reactive groups are capable of covalently bonding to more than one polymer molecule in the composition, the interaction of the reactive group between polymer molecules results in a cross-linking which forms the polymer three-dimensional matrix.

If desired the binding ligands in the formed polymer matrix may be derivatized, e.g., by noncovalently or covalently attaching the binding ligands either by the addition of a different binding ligand or chemical modification of the existing binding ligand, thereby further enabling the high capacity capture of a larger variety of target molecules. This binding ligand modification feature of the invention is illustrated in Examples 1, 6, 7 and 9 below.

In preparing the assay platforms of the invention the substrate may be contacted with an amount of a polymer composition to provide a polymer matrix having a density of at least 2 $\mu$g/cm$^2$. In a preferred embodiment the polymer composition is contacted with the substrate in an amount sufficient to provide a polymer matrix having a density of 4 $\mu$g/cm$^2$ to 30 $\mu$g/cm$^2$, e.g., 6 $\mu$g/cm$^2$ to 15 $\mu$g/cm$^2$.

Additionally, an amount of the polymer composition may be contacted with the substrate to provide a polymer matrix having a density of binding ligand of at least 1 nanomole/cm$^2$. In another embodiment the polymer matrix has a density of binding ligand of 1.2 nanomoles/cm$^2$ to 185 nanomoles/cm$^2$. In the most preferred embodiment the polymer matrix has a density of 1.5 nanomoles/cm$^2$ to 90 nanomoles/cm$^2$, e.g., 1.8 nanomoles/cm$^2$ to 15 nanomoles/cm$^2$.

In one embodiment of the assay platform of the instant invention the substrate is a multiwell polystyrene plate, the polymer molecules are dextran polymers, the binding ligand is a nickel chelate and the polymer matrix has a binding ligand density of 1.5 nanomoles/cm$^2$ to 7.5 nanomoles/cm$^2$. In other embodiments of the invention the binding ligand is a Gallium or Iron chelate or the binding ligand is glutathione.

In another embodiment of the invention the substrate is a multiwell polypropylene plate, the polymer molecules are dextran polymers, the binding ligand is an oligonucleotide. This binding ligand is prepared after the original matrix is formed on the substrate. In many cases when a higher molecular weight ligand is added to the original ligand on the matrix the ligand density will decrease due to the larger size of the new ligand.

In another embodiment of the invention the substrate is a multiwell polystyrene plate, the polymer molecules are dextran polymers, the binding ligand is streptavidin and the polymer matrix has a binding ligand density of 1.5 $\mu$g/cm$^2$ to 7.5 $\mu$g/cm$^2$. The binding ligand is prepared after the original matrix is formed on the substrate.

Finally, in another embodiment the invention has a substrate that is a multiwell polystyrene plate, the polymer molecules are dextran polymers, the binding ligand is selected from the group consisting of protein A, protein G, protein L or a mixture thereof, and the polymer matrix has a binding ligand density of 1.5 $\mu$g/cm$^2$ to 7.5 $\mu$g/cm$^2$. The binding ligand is prepared after the original matrix is formed on the substrate.

Produced examples described above in the assay platforms of the invention can be used to isolate target molecules from solutions containing the target molecules. For example, a multiwell plate having wells coated with the polymer matrix can be used to isolate target molecules from solution added to the individual wells of the plate. Once the solution is added to the plate, a period of time is allowed for the target molecule to react with the polymer matrix. As stated above the amount of time for reaction is a function of the target molecule, binding group, and the reason for using the plate. For example, if the plate is to be used as a quantitative measuring tool, the more time that is allowed for the binding molecule to react with the target molecule the greater the isolation of target molecule. If the plate is to be used as a purification format then the more time allowed for the binding molecule to react with the target molecule the greater the amount of target molecule isolated for characterization. If the plate is being used as a detection means, the amount of time that is allowed for the target molecule to react with the polymer matrix is less critical since it is the presence or absence of the target molecule that is important.

If the plate is being used as a quantitative measuring tool then the plate may be washed with water or a buffer after the target incubation period is completed. The amount of time before washing will vary according to the target molecule. In addition, the wash solution used, to remove unbound molecules from the plate, depends on the target molecule being isolated. For example, a hydrophobic solution would not be used to wash the plate if a hydrophobic ligand was employed on the polymer matrix, as it would remove the captured target molecule.

After washing, the target molecules that are covalently or noncovalently attached to the plate via the polymer matrix can either be disassociated from the plate and removed for characterization or quantitation, left on the surface to be detected using standard detection chemicals, or left on the surface as the new binding ligand to further react with biological or artificial samples to capture new target molecules followed by detection or characterization. If the molecules are to be disassociated from the plate the solvent used to disassociate the target molecules from the plate would depend on; the type of bonding between the target molecules and the attached binding ligand of the polymer matrix, and the selected method of analysis or characterization. For example, if the bond is electrostatic in nature then washing the plate with a solution of a particular ionic strength or pH may disassociate the target molecules from the plate. If the bond is hydrophobic in nature then the molecules can be disassociated from the plate by reagents that break hydrogen bonding, e.g., urea. If the bond is covalent in nature the target molecules can be disassociated from the plate by reagents and methods that break the covalent interaction. Dissociation may be accomplished by, but not limited to, chemical acid or base hydrolysis, proteolytic cleavage, and disulfide reduction.

If only detection of the target molecule is desired, the target molecules can be further reacted and detected while remaining attached to the binding ligands of the polymer matrix. In other words, the target molecules do not need to be disassociated from binding ligand or removed from the substrate surface.

Various detection molecules can be reacted with the target molecules. Some detection molecules used include specific antibodies, either unmodified or modified to have a reporter molecule such as a fluorescent probe or enzyme conjugates. The detection molecule used to react with the target molecules bound to the plate depend on the nature of the target molecules. For example, if the target molecule is a protein, then a fluorescently labeled antibody can be used for detection. Other molecules may use color changing molecules, e.g., antibody enzyme conjugates, to indicate the attachment to a bound target molecule. One skilled in the art would understand what type of molecule best could be used to detect the presence of the target molecule on the plate. The techniques for capture and analysis of target molecules are known to one of skill in the art and examples are reviewed by Ed Harlow and David Lane in, Antibodies, A Laboratory Manual, Cold Springs Harbor Laboratory, 1998, pp 1–726, hereby incorporated by reference.

By way of example, if the presence of a particular protein in the urine of a patient indicates that the patient has a particular medical condition, a fluorescently labeled antibody that binds to the target molecule can be incubated on the plate after urine has been exposed to the coated plate. If the target molecule was present in the urine, then that protein would bind to the binding ligand associated with the polymer matrix on the plate. After washing the wells to remove the unbound material, the antibody is applied to the target molecule bound to the substrate. Placing the plate containing the target molecule fluorescent antibody complex, in UV light revels the target molecule for a means of quantitatively measuring the disease state. The same can be accomplished using captured polynucleotides such as DNA and RNA fragments.

EXAMPLES

Example 1

Preparation of a High Capacity Nickel Chelate 96 Well Plate

Preparation of Dextran-Lysine: Periodate oxidized dextran was prepared by adding 2.5 g (0.014 moles) of dextran (average molecular weight of 3,368 kDa and range of 400 kDa to 54,000 kDa) into 31 mL of 0.05 M sodium acetate pH 5.0 buffer. The solution was stirred at room temperature until dissolved. The dextran was then cooled to 10° C. or lower in an ice bath. To the stirring dextran solution was added 3.6 mL of freshly prepared 0.45 M sodium periodate solution (1.7 mmoles). The reaction mixture was protected from light and allowed to stir in an ice bath for 2 hours. The periodate oxidized dextran solution was then slowly added to 75 mL of a solution of 1.5 M lysine (112.5 mmoles) supplemented with 5.6 mL of 200 proof ethanol and 1 mL of pyridine borane under reduced light. The reaction mixture was allowed to stir for 2 hours at room temperature while protected from light. Upon completion of the 2 hours, 5.83 mL of freshly prepared 2 M sodium borohydride was added to the reaction mixture and allowed to stir for 2 hours at room temperature. The reaction mixture was then transferred to dialysis tubing for continuous dialysis against running water for a minimum of 18 hours and then frozen and lyophilized to give a white fluffy solid (2.5 g) with an average molecular weight of 696 kDa, with a molecular weight range from 82 kDa to 11,000 kDa.

Preparation of Dextran-lysine-benzophenone: To 7.5 mL of 0.1 M sodium phosphate pH 7.0 buffer was added 0.30 g (0.14 mmole of amine) of dextran-lysine as prepared above and the mixture was stirred until homogeneous. 5.0 M hydrochloric acid was used to adjust the pH back to 7.0 upon dissolution. 2.6 mL of N,N-dimethylformamide (DMF) was then slowly added to the stirring solution, followed by 87 $\mu$L of a freshly prepared solution of a 12 mg/mL benzobenzoyl aminocaproic n-hydroxysuccinimide (NHS) ester in anhydrous DMF. The reaction was allowed to stir at room temperature while protected from light for 90 minutes. The material was dialyzed against water and lyophilized to give a stable dextran-lysine-benzophenone intermediate (0.30 g).

Preparation of Dextran-lysine-benzophenone-bis(N,N-carboxymethyl)cysteine: To a solution of 0.30 g of dextran-lysine-benzophenone as prepared above, before lyophilization, was slowly added 750 µl of a freshly prepared 200 mg/mL solution of maleimidobutyric acid NHS ester in DMF. The hazy reaction mixture was allowed to stir for 90 minutes at room temperature. To the stirring reaction mixture was added 63 µL of acetic anhydride. The reaction was stirred for 15 minutes at room temperature. Verification that all of the amines were blocked was determined using a fluorescamine assay. A constant volume ultrafiltration wash was performed on the reaction mixture representing a 10-fold wash with 0.1 M sodium phosphate pH 7.0 buffer. The washed reaction mixture was bubbled with argon for several minutes. To the washed reaction mix was added 351 µL of a freshly prepared solution of 100 mg/mL of bis (N,N'-carboxymethyl)cysteine ligand in 0.1 M sodium phosphate pH 7.0 buffer which was bubbled with argon. The reaction mixture was allowed to stir overnight at 2–8° C. while protected from light. The reaction mixture was dialyzed against running water overnight and then lyophilized to give a white fluffy solid (0.30 g).

Preparation of Dextran-lysine-bis (N,N'-carboxymethyl) cysteine: To 0.3 g dextran-lysine as prepared above, before lyophilization was added 750 µL of a freshly prepared 200 mg/mL solution of maleimidobutyric acid NHS ester in DMF was slowly added to the reaction mixture. The hazy reaction mixture was allowed to stir for 90 minutes at room temperature. To the stirring reaction mixture was added 63 µL of acetic anhydride. The reaction was stirred for 15 minutes at room temperature. Verification that all of the amines were blocked was determined using a fluorescamine assay. A constant volume ultrafiltration wash was performed on the reaction mixture representing a 10-fold wash with 0.1 M sodium phosphate pH 7.0 buffer. The washed reaction mixture was bubbled with argon for several minutes. To the washed reaction mixture was added 351 µL of a freshly prepared solution of 100 mg/mL of bis (N,N'-Carboxymethyl)cysteine ligand in 0.1 M sodium phosphate pH 7.0 buffer which was bubbled with argon. The reaction mixture was allowed to stir overnight at 2–8° C. The reaction mixture was dialyzed against running water overnight and then lyophilized to give a white fluffy solid (0.3 g).

Preparation of High Capacity Nickel Chelate 96 well plate: To 4 columns of a tissue culture treated (TCT) multiwell plate (96 well plate) was added 200 µL of a 0.15 mg/mL solution of dextran-lysine-benzophenone-bis (N,N'-carboxymethyl)cysteine in water (100/0). To 4 additional columns on the same TCT 96 well plate was added 200 µL of a 0.15 mg/mL in total dextran solution of 50% dextran-lysine-benzophenone-bis (N,N'-carboxymethyl)cysteine and 50% dextran-lysine-bis (N,N'-carboxymethyl)cysteine (50/50). The 96 well plate was allowed to dry overnight in an oven at 40° C. with air blowing over it. The dried 96 well plate was then photoirradiated for 32 minutes at approximately 9.0 mWatts/cm². The plate was then soaked overnight in 250 µL of water. The 96 well plate was then washed twice with 300 µL of water and loaded with 250 µL of a 3-(N-morpholino)butanesulfonic acid (MOPS) saline pH 7.0 containing 1 mM nickel sulfate hexahydrate and allowed to soak overnight at room temperature. After the target molecule nickel (59 daltons) is bound to the binding ligand the 96 well plates were then washed once with 300 µL of 0.05 M acetic acid, once with 300 µL of water, and then twice with 300 µL of MOPS pH 7.0 buffer.

Dextran Incorporation: The High Capacity Nickel Chelate 96 well plate, prepared as described above, was tested by determining the total dextran incorporation onto the 96 well plate. This data was achieved using an anthrone assay. To each section on the 96 well plate was added 200 µL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 1 below.

Protein Binding Capacity: The High Capacity Nickel Chelate 96 well plate, prepared as described above, was also tested by determining the total amount of 50 kDa target protein, recombinant metal chelating protein containing FLAG fusion peptide (FLAG-Bacterial Alkaline Phosphatase (FLAG-BAP)) that could be captured on the 96 well plate. A 0.15 mg/mL solution of a FLAG-BAP solution in Tris(hydroxymethyl)aminomethane buffered saline (TBS) pH 8.0 was incubated on the 96 well plate surface for 4 hours at room temperature. The FLAG-BAP was also substituted for either a 0.25 mg/mL solution of a 15 kDa synthetic ribonuclease (RNAse)-6-His-biotin or a 0.225 mg/mL solution of a 26 kDa histidine affinity tagged (HAT) fusion dihydrofolate reductase (DHFR) protein. After incubating for 4 hours, the 96 well plate was washed three times with 300 µL of phosphate buffered saline with Tween 20 (PBST), followed by three washes with 300 µL of water. A bicinchoninic acid (BCA) assay, using bovine serum albumin (BSA) as a standard, was run on the 96 well plate to determine the total amount of protein bound to the 96 well plate. The 96 well plate was read at $A_{560}$ against a BSA standard curve on the same 96 well plate in the blank wells to give the data as shown in table 1 below.

Purified FLAG-BAP (30 µg in 0.2 ml buffer per well) was added to all plates as described above. Bound FLAG-BAP was quantified directly on plate by BCA. Four different plates (A, B, C and D) were evaluated for protein binding capacity. Plate A comprised the assay platform of this invention. Plates B, C and D were commercially available plates with immobilized nickel used for capture, purification and detection of histidine containing proteins as follows: Plate B comprised Qiagen 35061 Ni-NTA HisSorb Plate, Plate C comprised the Pierce 15142 Reacti-Bind™ Metal Chelate Plate, clear strip plate and Plate D comprised the Pierce 15143 Reacti-Bind™ Metal Chelate Plate, High Binding Capacity. Only the Assay Platform of this invention gave any detectable signal using the BCA assay which was 10 µg protein bound per well (6.7 µg protein/cm²). Plates B, C and D, the commercial plates, produced no detectable signal by which to evaluate protein binding capacity. The lower limit of detection was 0.3 µg protein/well which was equivalent to 0.2 µg protein/cm². See, FIG. 1.

TABLE 1

Dextran Loading and Protein Binding Capacity

| | 50/50 | 100/0 |
|---|---|---|
| Total Net Dextran, (µg) | 7.30 | 8.17 |
| µg dextran/cm² | 4.77 | 5.33 |
| Expected Dextran, (µg/cm²) | 2.67 | 5.33 |

TABLE 1-continued

Dextran Loading and Protein Binding Capacity

| % Increase Relative to Expected Dextran | 178% | | A | | | |
|---|---|---|---|---|---|---|
| | Fusion protein | | RNAse-6-His-biotin | | HAT | |
| | 50/50 | 100/0 | 50/50 | 100/0 | 50/50 | 100/0 |
| Total Net Protein, (μg) | 6.42 | 5.00 | 4.51 | ND | 3.57 | ND |
| μg protein/cm² | 4.20 | 3.27 | 2.95 | ND | 2.33 | ND |
| Expected Total Net Protein, (μg/cm²) | 1.64 | 3.27 | ND | ND | ND | ND |
| % Increase Relative to Expected Protein | 257% | A | ND | ND | ND | ND |
| μg/cm² protein/μg/cm² dextran | 0.88 | 0.61 | 0.62 | ND | 0.49 | ND |

'A' represents the normalized value of 100%.
'ND' was information that was not determined at this time.

Specificity testing: To 4 wells in the 50/50 section of the 96 well plate was added 200 μL of crude *Escherichia coli* (*E. coli*) extract (approximately 5 mg/mL in total protein) which contained the desired recombinant metal chelating protein, FLAG-BAP. To 4 wells in the 50/50 section of the 96 well plate was added 200 μL of crude mammalian extract spiked to approximately 0.15 mg/mL with a recombinant metal chelating protein. To 4 wells in the same section of the 96 well plate was added 200 μL 0.15 mg/mL recombinant metal chelating protein in TBS pH 8.0. The wells were incubated overnight at 2–8° C. The 96 well plate was then washed 3 times with 300 μL PBST and 3 times with 300 μL of water. To each of the washed wells was added 200 μL of a 0.1 M imidazole solution in TBS pH 8.0. The 96 well plate was incubated on an orbital mixer for 30 minutes at room temperature. The eluted proteins were assayed for purity, both dilute and by a trichloroacetic acid (TCA) precipitation to represent the protein bound in an entire well, by sodium dodecyl sulfate polyacrylamide gel electrophoresis (SDS-PAGE). The gel demonstrated the specificity of binding from both *E. coli* and mammalian crude extracts because there was only a single band, equivalent to a purified recombinant metal chelating control protein.

Example 2
Preparation of a Hydrophobic 96 Well Plate

Preparation of Dextran Diaminohexane: The periodate oxidized solution (1.25 g) prepared as in Example 1 was added to 30 mL of a solution of 1.5 M diaminohexane, pH 8.5, supplemented with 5.6 mL 200 proof ethanol and 1 mL of pyridine borane. The reaction mixture was allowed to stir for 2 hours at room temperature while protected from light. Upon completion of the 2 hours, 2.95 mL of freshly prepared 2 M sodium borohydride was added to the reaction mixture and allowed to stir for 2 hours at room temperature. The reaction mixture was then transferred to dialysis tubing for continuous dialysis against running water for a minimum of 18 hours.

Preparation of Dextran-Diaminohexaneacetyl-Benzophenone: To 0.63 g of dialyzed dextran-diaminohexane was added 5.5 mL of a 0.5 M Sodium Phosphate pH 7.0 buffer followed by 180 μL of a 12 mg/mL benzobenzoyl aminocaproic NHS ester in anhydrous DMF with stirring. The reaction was allowed to stir at room temperature while protected from light for 90 minutes. To the stirring solution was added 400 μL (4.2 mmole) of acetic anhydride in 4 portions allowing 15 minutes of stirring in between each addition and a pH adjustment back to 7.0 with 5.0 M sodium hydroxide. Verification that all of the amines were blocked was determined using a fluorescamine assay. The reaction mixture was then dialyzed against running water overnight. The product was then frozen and lyophilized to give a white fluffy solid (0.6 g).

Preparation of Dextran-Diaminohexaneacetyl: To 0.63 g of the dialyzed dextran-diaminohexane solution was added 400 μL (4.2 mmole) of acetic anhydride in 4 portions allowing 15 minutes of stirring in between each addition along and a pH adjustment back to 7.0 with 5.0 M sodium hydroxide. Verification that all of the amines were blocked was determined using a fluorescamine assay. The reaction mixture was then dialyzed against running water overnight. The product was then frozen and lyophilized to give a white fluffy solid (0.6 g).

Preparation of a Hydrophobic 96 well plate: To 4 columns of a TCT 96 well plate was added 200 μL of either a 0.15 mg/mL or a 0.5 mg/mL solution of dextran-diaminohexaneacetyl-benzophenone in water (100/0). To 4 additional columns on the same TCT 96 well plate was added 200 μL of either a 0.15 mg/mL or 0.5 mg/mL in total dextran solution of 50% dextran-diaminohexaneacetyl-benzophenone and 50% dextran-diaminohexaneacetyl (50/50). To 4 additional columns on the same TCT 96 well plate was added 200 μL of a 0.5 mg/mL in total dextran solution of 75% dextran-diaminohexaneacetyl-benzophenone and 25% dextran-diaminohexaneacetyl (75/25). The 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of water. The 96 well plate was then washed twice with 300 μL of 0.3 M sodium chloride and twice with 300 μL of water.

Dextran Incorporation: The hydrophobic 96 well plate, prepared as described above, was tested by determining the total dextran incorporation onto the 96 well plate. This data was achieved using an anthrone assay. To each section on the 96 well plate was added 200 μL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 2 below.

Protein Binding Capacity: The Hydrophobic 96 well plate, prepared as described above, was also tested by determining the total amount of target protein that could be captured on the 96 well plate. A 1.0 mg/mL solution of the target molecule, albumin 66 kDa in 1.0 M sodium sulfate was incubated on the 96 well plate surface overnight at 2–8° C. The 96 well plate was washed three times with 1.0 M sodium sulfate. (A negative control 1.0 mg/mL solution of albumin in 0.005 M tris pH 8.0 was incubated on the 96 well plate surface overnight at 2–8° C. The 96 well plate was washed three times with 1.0 M Sodium Sulfate). A BCA assay was run on the 96 well plate to determine the total amount of protein bound to the 96 well plate. The 96 well plate was read at $A_{560}$ against a BSA standard curve on the same 96 well plate in the blank wells to give the data as shown in table 2 below.

TABLE 2

| | Hydrophobic Plate | | | | |
|---|---|---|---|---|---|
| | 0.15 mg/mL dextran load | | 0.5 mg/mL dextran load | | |
| | 50/50 | 100/0 | 50/50 | 75/25 | 100/0 |
| Total Net Dextran, (μg) | 3.91 | 6.26 | 3.779 | 9.109 | 19.360 |
| μg dextran/(cm²) | 2.56 | 4.09 | 2.47 | 5.95 | 12.65 |
| Expected Dextran, (μg) | 2.05 | 4.09 | 6.33 | 9.49 | 12.65 |
| % Increase Relative to Expected Dextran | 125% | A | −61% | −37% | A |
| Total Net Protein (μg) | ND | ND | 0.07 | 0.2 | 0.3 |
| μg protein/(cm²) | ND | ND | 0.046 | 0.13 | 0.20 |
| Expected Total Net Protein (μg/cm²) | ND | ND | 0.10 | 0.15 | 0.20 |
| % Increase Relative to Expected Protein | ND | ND | −54% | −13% | A |
| μg/cm² protein/μg/cm² dextran | ND | ND | 0.019 | 0.022 | 0.022 |

'A' represents the normalized value of 100%.
'ND' was information that was not determined at this time.

Example 3

Preparation of a Dextran-Iminobispropylamine Anion Exchange 96 Well Plate

Preparation of Dextran-Iminobispropylamine: The periodate oxidized dextran solution (1.25 g) prepared as above in example 1 was added to 30 mL of a solution of 1.5 M, pH 8.5, iminobispropylamine supplemented with 5.6 mL 200 proof ethanol and 1 mL of pyridine borane. The reaction mixture was allowed to stir for 2 hours at room temperature while protected from light. Upon completion of the 2 hours, 2.95 mL of freshly prepared 2.0 M sodium borohydride was added to the reaction mixture and allowed to stir for 2 hours at room temperature. The reaction mixture was then transferred to dialysis tubing for continuous dialysis against running water for a minimum of 18 hours. The dialyzed dextran-iminobispropylamine was frozen and lyophilized to give a white fluffy solid (1.25 g).

Preparation of Dextran-Iminobispropylamine-Benzophenone: To 44 mL of a 14 mg/mL solution of dextran-iminobispropylamine in water was added 4.4 mL of a 0.5 M sodium phosphate pH 7.0 buffer followed by the addition of 180 μL of a 12 mg/mL bezobenzoyl aminocaproic NHS ester in anhydrous DMF with stirring. The reaction was allowed to stir at room temperature while protected from light for 90 minutes. The reaction mixture was then dialyzed against running water overnight. The product was then frozen and lyophilized to give a white fluffy solid (0.6 g).

Preparation of an Anion Exchange 96 well plate: To 4 columns of a TCT 96 well plate was added 200 μL of either a 0.15 mg/mL or a 0.5 mg/mL solution of dextran-iminobispropylamine-benzophenone in water (100/0). To 4 additional columns on the same TCT 96 well plate was added 200 μL of either a 0.15 mg/mL or 0.5 mg/mL in total dextran solution of 50% dextran-iminobispropylamine-benzophenone and 50% dextran-iminobispropylamine (50/50). To 4 additional columns on the same TCT 96 well plate was added 200 μL of a 0.5 mg/mL in total dextran solution of 75% dextran-iminobispropylamine-benzophenone and 25% dextran-iminobispropylamine (75/25). The 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of water. The 96 well plate was then washed twice with 300 μL of 0.3 M sodium chloride and twice with 300 μL of water.

Dextran Incorporation: The anion exchange 96 well plate, prepared as described above, was tested by determining the total dextran incorporation onto the 96 well plate. This data was achieved using an anthrone assay. To each section on the 96 well plate was added 200 μL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 3 below.

Protein Binding Capacity: The Anion Exchange 96 well plate, prepared as described above, was also tested by determining the total amount of protein that could be captured on the 96 well plate. A 1.0 mg/mL solution of albumin in 0.005 M tris(hydroxymethyl)aminomethane (tris) pH 8.0 incubated on the 96 well plate surface overnight at 2–8° C. The 96 well plate was washed several times with 0.005 M tris. (A negative control was a 1.0 mg/mL solution of albumin in 0.005 M tris pH 8.0 containing 0.5 M sodium chloride incubated on the 96 well plate surface overnight at 2–8° C. The 96 well plate was washed several times with 0.005 M tris pH 8.0.) A BCA assay was run on the 96 well plate to determine the total amount of protein bound to the 96 well plate. The 96 well plate was read at $A_{560}$ against a BSA standard curve on the same 96 well plate in the blank wells to give the data as shown in table 3 below.

TABLE 3

| | Anion Exchange Plate | | | | |
|---|---|---|---|---|---|
| | 0.15 mg/mL dextran load | | 0.5 mg/mL dextran load | | |
| | 50/50 | 100/0 | 50/50 | 75/25 | 100/0 |
| Total Net Dextran, (μg) | 1.63 | 1.25 | 1.62 | 1.36 | 1.39 |
| μg dextran/(cm²) | 1.07 | 0.82 | 1.06 | 0.89 | 0.91 |
| Expected Dextran, (μg/cm²) | 0.41 | 0.82 | 0.45 | 0.68 | 0.91 |
| % Increase Relative to Expected Dextran | 261% | A | 233% | 131% | A |
| Total Net Protein (μg) | 1.0 | 1.0 | 1.3 | 1.4 | 1.3 |
| μg protein/(cm²) | 0.65 | 0.65 | 0.85 | 0.92 | 0.85 |
| Expected Total Net Protein (μg/cm²) | 0.33 | 0.65 | 0.43 | 0.64 | 0.85 |
| % Increase Relative to Expected Protein | 50% | A | 200% | 144% | A |
| μg protein/μg dextran | 0.61 | 0.80 | 0.80 | 1.03 | 0.94 |

'A' represents the normalized value of 100%.
'ND' was information that was not determined at this time.

Example 4
Preparation of a Dextran-Lysine Anion Exchange 96 Well Plate

Preparation of an Anion Exchange 96 well plate: To 4 columns of a TCT 96 well plate was added 200 μL of either a 0.15 mg/mL or a 0.5 mg/mL solution of dextran-lysine-benzophenone (as prepared in example 1) in water (100/0). To 4 additional columns on the same TCT 96 well plate was added 200 μL of either a 0.15 mg/mL or 0.5 mg/mL in total dextran solution of 50% dextran-lysine-benzophenone and 50% dextran-lysine (50/50) (as prepared in example 1). To 4 additional columns on the same TCT 96 well plate was added 200 μL of a 0.5 mg/mL in total dextran solution of 75% dextran-lysine-benzophenone and 25% dextran-lysine (75/25). The 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of water. The 96 well plate was then washed twice with 300 μL of 0.3 M sodium chloride and twice with 300 μL of water.

Dextran Incorporation: The anion exchange 96 well plate, prepared as described above, was tested by determining the total dextran incorporation onto the 96 well plate. This data was achieved using an anthrone assay. To each section on the 96 well plate was added 200 μL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 4 below.

Protein Binding Capacity: The Anion Exchange 96 well plate, prepared as described above, was also tested by determining the total amount of protein that could be captured on the 96 well plate. A 1.0 mg/mL solution of the target molecule, albumin in 0.005 M tris pH 8.0 incubated on the 96 well plate surface overnight at 2–8° C. The 96 well plate was washed 3 times with 0.005 M tris pH 8.0. A negative control was a 1.0 mg/mL solution of albumin in 0.005 M tris pH 8.0 containing 0.5 M sodium chloride incubated on the 96 well plate surface overnight at 2–8° C., the 96 well plate was washed several times with 0.005 M tris pH 8.0. A BCA assay was run on the 96 well plate to determine the total amount of protein bound to the 96 well plate. The 96 well plate was read at $A_{560}$, against a BSA standard curve on the same 96 well plate in the blank wells to give the data as shown in table 4 below.

TABLE 4

| | Ion Exchanger 96 Well Plate | | | | |
|---|---|---|---|---|---|
| | 0.15 mg/mL dextran load | | 0.5 mg/mL dextran load | | |
| | 50/50 | 100/0 | 50/50 | 75/25 | 100/0 |
| Total Net Dextran, (μg) | 3.36 | 5.08 | 3.47 | 9.11 | 12.93 |
| μg dextran/cm² | 2.20 | 3.32 | 2.27 | 5.95 | 8.45 |
| Expected Dextran, (μg/cm²) | 2.55 | 5.08 | 4.23 | 6.34 | 8.45 |
| % Increase Relative to Expected Dextran | 132% | A | −46% | −6% | A |
| Total Net Protein (μg) | ND | ND | 0.9 | 1.0 | 2.8 |
| μg protein/cm² | ND | ND | 0.59 | 0.65 | 1.83 |
| Expected Total Net Protein (μg/cm²) | ND | ND | 0.92 | 1.37 | 1.83 |
| % Increase Relative to Expected Protein | ND | ND | −36% | −53% | A |

TABLE 4-continued

| | Ion Exchanger 96 Well Plate | | | | |
|---|---|---|---|---|---|
| | 0.15 mg/mL dextran load | | 0.5 mg/mL dextran load | | |
| | 50/50 | 100/0 | 50/50 | 75/25 | 100/0 |
| μg/cm² protein/ μg/cm² dextran | ND | ND | 0.26 | 0.11 | 0.22 |

'A' represents the normalized value of 100%.
'ND' was information that was not determined at this time.

Example 5
Preparation of a Cation Exchange 96 Well Plate

Preparation of Dextran-lysine-benzophenone-succinylate: Dextran-lysine (0.63 g), as prepared in example 1, was dissolved in 44 mL of 0.05 M sodium phosphate pH 7.0 buffer. To the buffered dialyzed dextran-lysine-benzophenone solution was slowly added 180 μL of a 12 mg/mL benzobenzoyl aminocaproic NHS ester in anhydrous DMF with stirring. The reaction was allowed to stir at room temperature while protected from light for 90 minutes. To the stirring reaction mixture was added 4.2 mmole succinyl anhydride in 2 portions allowing 15 minutes of stirring in between each addition and pH adjustment back to 7.0 with 5.0 M sodium hydroxide. A fluorescamine assay indicated that all of the free amines on the dextran-lysine were not completely blocked with a succinate group. Ali additional 1.6 mL of 100 mg/mL of succinyl anhydride was added, stirred for 15 minutes and the pH was adjusted to 7.0. 100 μL of acetic anhydride was then added to the stirring reaction mixture and allowed to stir for 10 minutes. The pH was then adjusted back to 7.0 and the fluorescamine assay indicated that the free amines were no longer present in the sample. The reaction mixture was then dialyzed against running water overnight. The product was then filtered through 0.45 micron filter, frozen, and lyophilized to give a white fluffy solid (0.60 g).

Preparation of Dextran-Lysine-succinylate: Dextran-lysine (0.63 g), as prepared in example 1, was dissolved in 44 mL of 0.1 M sodium phosphate pH 7.0 buffer. To this solution was added 4.2 mmole succinyl anhydride in 2 portions as above. A fluorescamine assay indicated that all of the free amines on the dextran-lysine were not completely blocked with a succinate group. An additional 1.6 mL of 100 mg/mL of succinyl anhydride was added, stirred for 15 minutes and the pH was adjusted to 7.0. 100 μL of acetic anhydride was also added to the stirring reaction mixture and allowed to stir for 10 minutes. The pH was then adjusted back to 7.0 and the fluorescamine assay indicated that the free amines were no longer present in the sample. The reaction mixture was then dialyzed against running water overnight. The product was then filtered through 0.45 micron filter, frozen and lyophilized to give a white fluffy solid (0.060 g).

Preparation of a Cation Exchange 96 Well Plate: To 4 columns of a TCT 96 well plate was added 200 μL of either a 0.15 mg/mL or a 0.5 mg/mL solution of dextran-lysine-benzophenone-succinylate in water (100/0). To 4 additional columns on the same TCT 96 well plate was added 200 μL of either a 0.15 mg/mL or 0.5 mg/mL in total dextran solution of 50% dextran-lysine-benzophenone-succinylate and 50% dextran-lysine-succinylate (50/50). To 4 additional columns on the same TCT 96 well plate was added 200 μL of a 0.5 mg/mL in total dextran solution of 75% dextran-lysine-benzophenone-succinylate and 25% dextran-lysine-succinylate (75/25). The 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of water. The 96 well plate was then washed twice with 300 μL of 0.3 M sodium chloride and twice with 300 μL of water.

Dextran Incorporation: The cation exchange 96 well plate, prepared as described above, was tested by determining the total dextran incorporation onto the plate. This data was achieved using an anthrone assay. To each section on the 96 well plate was added 200 μL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 5 below.

Protein Binding Capacity: The cation exchange 96 well plate, prepared as described above, was also tested by determining the total amount of protein that could be captured on the 96 well plate. A 1.0 mg/mL solution of the 68 kDa target protein, avidin, in 0.005 M acetic acid pH 5.0 incubated on the 96 well plate surface overnight at 2–8° C. The 96 well plate was washed several times with 0.005 M acetic acid. A negative control was a 1.0 mg/mL solution of avidin in 0.005 M acetic acid pH 5.0 containing 0.5 M sodium chloride incubated on the 96 well plate surface overnight at 2–8° C. The 96 well plate was washed several times with 0.005 M acetic acid pH 8.0. A BCA assay was run on the 96 well plate to determine the total amount of protein bound to the 96 well plate. The 96 well plate was read at $A_{560}$ against a BSA standard curve on the same 96 well plate in the blank wells to give the data as shown in table 5 below.

TABLE 5

| | Cation Exchange 96 Well Plate | | | | |
|---|---|---|---|---|---|
| | 0.15 mg/mL dextran load | | 0.5 mg/mL dextran load | | |
| | 50/50 | 100/0 | 50/50 | 75/25 | 100/0 |
| Total Net Dextran, (μg) | 2.75 | 5.95 | 3.59 | 4.52 | 11.27 |
| μg dextran/(cm²) | 1.80 | 3.89 | 2.35 | 2.95 | 7.37 |
| Expected Dextran, (μg/cm²) | 1.95 | 3.89 | 3.69 | 5.53 | 7.37 |
| % Increase Relative to Expected Dextran | −7% | A | −36% | −47% | A |
| Total Net Protein (μg) | 2.8 | 6.1 | 6.3 | 8.3 | 17.5 |
| μg protein/cm² | 1.83 | 3.99 | 4.12 | 5.42 | 11.44 |
| Expected Total Net Protein (μg/cm²) | 2.00 | 3.99 | 5.72 | 8.58 | 11.44 |

TABLE 5-continued

Cation Exchange 96 Well Plate

|  | 0.15 mg/mL dextran load | | 0.5 mg/mL dextran load | | |
| --- | --- | --- | --- | --- | --- |
|  | 50/50 | 100/0 | 50/50 | 75/25 | 100/0 |
| % Increase Relative to Expected Protein | −9% | A | −28% | −37% | A |
| μg protein/μg dextran | 1.02 | 1.03 | 1.75 | 1.84 | 1.56 |

'A' represents the normalized value of 100%.
'ND' was information that was not determined at this time.

Example 6
Preparation of a S-Acetylthioglycolic Acid Reactive 96 Well Plate

Preparation of Dextran-lysine-benzophenone-s-acetylthioglycolic acid: To 7.6 mL of 0.1 M sodium phosphate pH 7.0 buffer was added 0.30 g of dextran-lysine as prepared in example 1 and the mixture was stirred until homogeneous. 5 M hydrochloric acid was used to adjust the pH back to 7.0 upon dissolution. 2.6 mL of N,N-dimethylformamide (DMF) was then slowly added to the stirring solution followed by 87 μL of a freshly prepared solution of a 12 mg/mL benzobenzoyl aminocaproic n-hydroxysuccinimide (NHS) ester in anhydrous DMF. The reaction was allowed to stir at room temperature while protected from light for 90 minutes. Upon completion of the 90 minutes, 775 μL of a freshly prepared 200 mg/mL solution of s-acetylthioglycolic acid (SATA) NHS ester in DMF was slowly added to the reaction mixture. The hazy reaction mixture was allowed to stir for 90 minutes at room temperature. To the stirring reaction mixture was added 63 μL of acetic anhydride. The reaction was stirred for 15 minutes at room temperature. Verification that all of the amines were blocked was determined using a fluorescamine assay. The reaction mixture was dialyzed against running water overnight and then lyophilized to give a white fluffy solid (0.30 g).

Preparation of Dextran-lysine-s-acetylthioglycolic acid: To 7.6 mL of 0.1 M sodium phosphate pH 7.0 buffer was added 0.30 g of dextran-lysine as prepared in example 1 and the mixture was stirred until homogeneous. 5.0 M hydrochloric acid was used to adjust the pH back to 7.0 upon dissolution. 2.6 mL of N,N-dimethylformamide (DMF) was then slowly added to the stirring solution followed by 775 μL of a freshly prepared 200 mg/mL solution of SATA NHS ester in DMF was slowly added to the reaction mixture. The hazy reaction mixture was allowed to stir for 90 minutes at room temperature. To the stirring reaction mixture was added 6 μL of acetic anhydride. The reaction was stirred for 15 minutes at room temperature. Verification that all of the amines were blocked was determined using a fluorescamine assay. The reaction mixture was dialyzed against running water overnight and then lyophilized to give a white fluffy solid (0.30 g).

Preparation of a S-Acetylthioglycolic Acid Reactive 96 well plate (A): To a TCT 96 well plate was added 200 μL of a 0.1 mg/mL solution dextran-lysine-benzophenone-s-acetylthioglycolic acid in water (100/0). The 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of 10 mM MOPS containing 0.15 M sodium chloride. The 96 well plate was then washed three times with 300 μL of 10 mM MOPS containing 0.15 M sodium chloride and three times with 300 μL of water.

Preparation of a S-Acetylthioglycolic Acid Reactive 96 well plate (B): To 4 columns of a High Binding 96 well plate was added 200 μL of a 0.15 mg/mL solution of dextran-lysine-benzophenone-s-acetylthioglycolic acid in water (100/0). To 4 additional columns on the same High Binding 96 well plate was added 200 μL of a 0.15 mg/mL in total dextran solution of 50% dextran-lysine-benzophenone-s-acetylthioglycolic acid and 50% dextran-lysine-s-acetylthioglycolic acid (50/50). the 96 well plate was allowed to dry overnight in an oven at 40° C. with air blowing over it. The dried 96 well plate was then photoirradiated for 32 minutes at approximately 9.0 mWatts/cm². The 96 well plate was then soaked overnight in 300 μL of 0.025 M sodium acetate. The 96 well plate was then washed three times with 300 μL of 0.025 M sodium acetate and twice with 300 μL of water.

Dextran Incorporation: The S-Acetylthioglycolic Acid reactive 96 well plate (B), prepared as described above, was tested by determining the total dextran incorporation onto the 96 well plate. This data was achieved using an anthrone assay. To each section on the 96 well plate was added 200 μL of an anthrone reagent. The 96 well plate was heated in an oven at 80–85° C. for 30 minutes to develop the color. The 96 well plate was read at $A_{620}$ against a dextran standard curve on the same 96 well plate in the blank wells to give the data as shown in table 6 below.

TABLE 6

S-Acetylthioglycolic Acid Reactive Plate

|  | 0.15 mg/mL dextran load | |
| --- | --- | --- |
|  | 50/50 | 100/0 |
| Total Net Dextran, (μg) | 7.7 | 12.8 |
| μg dextran/(cm²) | 5.03 | 8.37 |
| Expected Dextran, (μg) | 4.19 | 8.37 |
| % Increase Relative to Expected Dextran | 120% | A |

'A' represents the normalized value of 100%

Ligand Density: The SATA ligand density of the plate (B) was estimated to be 1.56 and 2.60 nmoles/cm² for the 50/50 and 100/0 matrices respectively.

Example 7
Preparation of the Streptavidin Coated 96 Well Plate

Preparation of the Streptavidin Coated 96 Well Plate (A): The S-Acetylthioglycolic Acid reactive 96 well plate (A), as prepared in example 6, was used to prepare a streptavidin coated 96 well plate. To all of the wells on the coated 96 well plate was added 200 μL of a 0.1 M solution of hydroxylamine in 0.1 M sodium phosphate pH 6.5. The 96 well plate was incubated at room temperature for 5 minutes with rapid orbital mixing. The 96 well plate was aspirated.

200 μL of a 0.1 mg/mL solution of the 60 kDa target molecule, streptavidin-maleimide in 0.1 M sodium phosphate pH 7.0 bubbled with argon was added to half of the S-Acetylthioglycolic Acid plate, 48 wells, and 200 μL of a 0.05 mg/mL solution of streptavidin-maleimide was added to the remaining 48 wells. The 96 well plate was allowed to incubate in a cold room overnight to allow covalent attachment. The supernatant of several wells were combined and a Bradford assay was performed to determine that about 50% of the streptavidin-maleimide was covalently attached to the plate. The binding was calculated to be 3.3 and 6.67

μg streptavidin/cm² for the 0.05 and 0.1 mg/mL solutions, respectively. The plate was then washed 3 times with 300 uL of 0.1 M sodium phosphate pH 7.0 and 200 μL of 1.0 mM β-mercaptoethanol in 0.1 sodium phosphate was added to react with free maleimide at room temperature for 15 minutes with orbital mixing. The plate was then washed three times with 300 μL of 0.1 M sodium phosphate pH 7.0 then 200 μL of 1.0 mM bromoacetic acid in 0.1 M sodium phosphate pH 7.0 added and was allowed to incubate for 1 hour at room temperature with orbital mixing to block free sulfhydryls. The streptavidin plates were then washed 3 times with 300 μL of water and dried.

Preparation of the Streptavidin Coated 96 Well Plate (B): The S-Acetylthioglycolic Acid reactive 96 well plate (B), as prepared in example 6, was used to prepare a streptavidin coated 96 well plate. To all of the wells on the coated 96 well plate was added 200 μL of a 0.05 M solution of hydroxylamine in 0.15 M sodium chloride, 0.02 M sodium phosphate, 0.001 M ethylenediaminetetraacetic acid (EDTA) pH 6.8. The 96 well plate was incubated at room temperature for 45 minutes with rapid orbital mixing. The 96 well plate was aspirated.

200 μL of a 0.05 mg/mL solution of streptavidin-maleimide in 0.15 M sodium chloride, 0.02 M sodium phosphate, 0.001 M EDTA pH 6.8 was then added to each rows 2–4 and 8–10. The 96 well plate was allowed to incubate at room temperature with orbital mixing for 4 hours and then in the cold room overnight. The supernatant of several wells were combined and the $A_{280}$ was read as it compares to a buffer blank and to a solution of 0.05 mg/mL streptavidin maleimide as loaded onto the 96 well plate. The results showed 4.18 and 4.38 μg streptavidin/cm² for 50/50 and 100/0, respectively.

Protein Binding Capacity: To a streptavidin coated plate as prepared above in (A) was added a 0.15 mg/mL solution of biotin-bovine serum albumin (BSA) in PBS. The plate was allowed to incubate at room temperature for 1 hour with orbital mixing. A Bradford assay was run and demonstrated 1.13 and 1.76 μg biotinylated albumin/cm² for the 3.3 and 6.67 μg streptavidin/cm² plates, respectively.

Biotinylated Oligo Binding Capacity: Initially specificity of binding was determined by adding a 1.3 μM solution of 5'-biotin-dT10-fluorescein-3' in PBS to the streptavidin plates prepared above (A) with varying concentrations free biotin and allowed to incubate for 15 minutes at room temperature. The plates were then washed and the fluorescence of any bound 5'-biotin-dT10-fluorescein-3' was determined on a plate reader. The results indicate that the free biotin will inhibit the binding to the streptavidin plate demonstrating specific affinity of the binding ligand. Secondly, various concentrations of 5'-biotin-dT10-fluorescein-3" in PBS, ranging from 0–10 μM were added to the plate in the absence of free biotin and allowed to incubate for 15 minutes at room temperature. The plates were then washed and the fluorescence of any bound 5'-biotin-dT10-fluorescein-3' was read on a plate reader. The results indicated that the wells were saturated with 5'-biotin-dT10-fluorescein-3' at a concentration of approximately 2.5 μM. The binding of the 5'-biotin-dT10-fluorescein-3', the new binding ligand, was determined using anti-FITC antibody as the target molecule.

Example 8

Preparation of a Nickel Chelate Coated Matrix Assisted Laser Desorption Ionization (MALDI) Plate Preparation of Nickel Chelate MALDI plate: A stainless steel MALDI plate containing 20 individual sample spots, previously cleaned with methanol, was dipped into a 1 mg/mL solution of parafilm dissolved in chloroform. To the coated MALDI plate was added 3 μL of a 0.75 mg/mL in total dextran solution of 50% dextran-lysine-benzophenone-bis (N, N'-carboxymethyl) cysteine (average molecular weight of 1,117 kDa and range of 112 kDa to 19,220 kDa) and 50% dextran-lysine-bis (N,N'-carboxymethyl)cysteine (average molecular weight of 696 kDa and range of 82 kDa to 11,080 kDa) as prepared in example 1. The MALDI plate was allowed to dry for 30 minutes with air blowing over it. The dried MALDI plate was then photoirradiated for 32 minutes at approximately 9.0 mWatts/cm². The MALDI plate was then soaked with the target molecule by applying 3 μL of a 0.01 M nickel sulfate solution in water for 30 minutes at 2–8° C. The target was stored in the cooler to help prevent evaporation. The MALDI plate was then soaked in water for 20 minutes.

Protein capture a Nickel Chelate MALDI plate: The MALDI plate containing the matrix with nickel chelate binding ligand was incubated with 3 μL per sample spot of a 0.5 mg/mL solution of the target molecule FLAG-BAP with and without the presence of cude E. coli extract in TBS pH 8.0 for 4 hours at 2–8° C. The MALDI plate was incubated in the cooler to help prevent evaporation. The MALDI plate was then soaked in 0.01 M ammonium bicarbonate for 20 minutes. The MALDI plate was dried in a MALDI plate drier. Sinapinic acid in 70% acetonitrile, 0.1% trifluoroacetic acid (TFA) was then added to each sample spot on MALDI plate and dried. Analysis was done using a Kratos Kompact Discovery SEQ MALDI-TOF mass spectrometer. Results from the study indicate that the FLAG-BAP protein was detected and found to be pure whether captured from the purified or crude samples. In addition, the FLAG-BAP protein was not detected on the MALDI plate that was soaked for 30 minutes in TBS pH 8.0 containing 100 mM imidazole prior to the 0.01 M ammonium bicarbonate soak, demonstrating the specificity of the affinity capture.

Synthetic protein capture on a Nickel Chelate MALDI plate: The MALDI plate was incubated with 3 μL per sample spot of a 0.5 mg/mL solution of a chemically synthesized 15 kDa target molecule, RNAse-6-His-biotin in TBS pH 8.0 for 4 hours at 2–8° C. The MALDI plate was stored in the cooler to help prevent evaporation. Upon completion of the 4 hour incubation time, the MALDI plate was soaked in 0.01 M ammonium bicarbonate for 20 minutes. The MALDI plates were dried in a MALDI plate drier and then 1 μL sinapinic acid in 70% acetonitrile, 0.1% TFA was then added directly to each sample spot of the MALDI plate and dried. Analysis was done using a Kratos Kompact Discovery SEQ MALDI-TOF mass spectrometer. Results from the study demonstrate that the RNAse-6-His-biotin was captured. In addition, the RNAse-6-His-biotin was not detected on the MALDI plate that was soaked for 30 minutes in TBS pH 8.0 containing 100 mM imidazole prior to the 0.01 M ammonium bicarbonate soak.

Peptide capture on a Nickel Chelate MALDI plate: The MALDI plate was incubated with 3 μL per sample spot of a 0.1 mg/mL solution of a 3.2 kDa synthetic polypeptide target molecule, histidine containing peptide with a biotin tag in TBS pH 8.0 for four hours at 2–8° C. The MALDI plate was stored in the cooler to help prevent evaporation. Upon completion of the 4 hour incubation time, the MALDI plate was dipped in water to remove unbound material. To some of the sample spots on the MALDI plate was added 2 μL of a 0.1 mg/mL solution of streptavidin with and without 0.1 mg/mL biotin in TBS pH 8.0. The MALDI plate was allowed to incubate at 2–8° C. for 2 hours. The MALDI plate was then soaked in TBS pH 8.0 containing 0.5 M sodium chloride for 20 minutes followed by 0.01 M ammonium bicarbonate for 20 minutes. The MALDI plate was dried in a plate drier and then 1 μL α-cyano-4-hydroxycinnamic acid in 70% acetonitrile, 0.1% TFA was then added to the sample spots containing peptide, sinapinic acid was used in place of α-cyano-4-hydroxycinnamic acid for spots containing peptide plus streptavidin. The MALDI plate was dried. Analysis was done using a Kratos Kompact Discovery SEQ MALDI-TOF mass spectrophotometer. Results from the study indicate that the peptide was detected in all cases, showing high affinity for the chelate binding ligand. In addition, streptavidin was detected in wells that were incubated without the presence of free biotin showing that the newly formed "chelate histidine containing peptide with a biotin tag" binding ligand has streptavidin affinity capture properties.

Example 9
Porosity Study of High Capacity Nickel Chelate Plate

Porosity study: A high capacity nickel chelate 96 well plate was prepared, as give in example 1, using 0.2 mL of a mixture of one part dextran-lysine-benzophenone-bis (N,N'-carboxymethyl)cysteine and one part dextran-lysine-bis (N,N'-carboxymethyl)cysteine (50/50) at a 0.2 mg/mL and a 0.4 mg/mL in water. The average molecular weight of the polymers was 737 kDa and range of 300 kDa to 10,000 kDa).

200 μL of a 0.15 mg/mL solution of FLAG-BAP protein was added to 9 wells in each section of the plate and allowed to incubate in the cold room overnight. The next morning, the plate was washed 3 times on an automated plate washer with 300 μL of PBST. At that point, 200 μL of a 25 μg/mL solution of a 150 kDa mouse monoclonal antibody, Anti-FLAG® M2 (Sigma Product Code F3165), was added to 6 of the wells and allowed to incubate at room temperature for 5 hours to allow the antibody to bind to the FLAG-BAP protein, washed 3 times on an automated washer with 300 μL of PBST. The Anti-FLAG® M2 step was repeated because the wells were not saturated the first time due to high binding capacity. 200 μL of a 100 μg/mL solution of Anti-FLAG® M2 was added and allowed to incubate overnight in the cold room. The plate was washed 3 times on an automated plate washer with PBST. Finally, 200 μL of 100 μg/mL solution of a 150 kDa anti-mouse IgG FITC conjugate was added to 3 of the wells that contained the protein protein interaction complex consisting of the FLAG-BAP protein and the Anti-FLAG® M2. This was allowed to incubate for 2 hours at room temperature without shaking and 1 hour at room temperature with shaking to assure binding of the anti-mouse IgG FITC conjugate to the Anti-FLAG® M2. The plate was then washed 3 times on an automated plate washer with 300 μL of PBST. The BCA reagent was allowed to develop for 1 hour at 37° C. and then the $A_{560}$ was determined on a plate reader. The overall results indicate that there was no restriction in porosity up to 350 kDa.

Example 10
Preparation of the Anti-FLAG® M2 Coated 96 Well Plate

Preparation of—Anti-FLAG® M2 Maleimide Conjugate: To 1 mL of a 4.4 mg/mL solution of Anti-FLAG® M2 in PBS was added 0.5 mL of 0.2 M sodium phosphate buffer pH 6.7. To the stirring solution was added 10 μL of a 0.03 μmoles/μL solution of maleimidocaproic acid NHS ester in anhydrous DMF. The solution was allowed to incubate for 1 hour at room temperature and desalted on a Sephadex G50 column. The fractions were monitored by $A_{280}$ to give product in fractions 4–6, which gave 2.8 mL of product at approximately 1.3 mg/mL.

Preparation of the Anti-FLAG® M2 Coated 96 Well Plate: To the SATA reactive 96 well plate (A), as prepared in example 6, was added 200 μL of a 0.1 M solution of hydroxylamine in 0.1 M sodium phosphate pH 6.5. The 96 well place was incubated at room temperature for 5 minutes with rapid orbital mixing. The 96 well plate was washed 3 times with 300 μL of 0.1 M sodium phosphate buffer pH 7.0 which was bubbled with argon.

200 μL of a 0.15 mg/mL solution of Anti-FLAG® M2 maleimide conjugate, as prepared above, 0.1 M sodium phosphate pH 7.0 which was bubbled with argon, was then added to each well in 2 columns on the plate. The columns on the plate that were not incubated with the Anti-FLAG® M2 maleimide conjugate were control wells for assaying purposes. The 96 well plate was allowed to incubate at room temperature with orbital mixing for 4 hours and then in the cold room overnight. The 96 well plate was then washed 3 times with 200 μL of 0.1 M sodium phosphate pH 7.0. 200 μL of a 1.0 mM β-mercaptoethanol solution in 0.1 M sodium phosphate pH 7.0 was added to the wells that were previously incubated with Anti-FLAG M2 maleimide conjugate and allowed to incubate for 15 minutes at room temperature with orbital mixing. The plate was then washed 3 times with 0.1 M sodium phosphate buffer pH 7.0. To one column that was incubated with Anti-FLAG M2 maleimide conjugate and one column that was not incubated with Anti-FLAG® M2 maleimide conjugate was loaded with 200 μL of a 1.0 mM bromoacetic acid solution in 0.1 M sodium phosphate pH 7.0 and allowed to incubate at room temperature for 1 hour with orbital mixing. The wells that were not loaded with the bromoacetic acid solution were control wells for assaying purposes. The plates were then washed 3 times with 300 μL of water.

Incorporation of Anti-FLAG® M2 on the 96 well plate: The Anti-FLAG® M2 plate, prepared as described above, was tested by determining the total protein that was captured on the SATA reactive 96 well plate. A BCA assay was run to determine the amount of Anti-FLAG® M2 that was captured on the plate with the remaining free sulfhydryl groups blocked and not blocked with bromoacetic acid, and against the wells that were not incubated with Anti-FLAG® M2 that were blocked and not blocked with bromacetic acid. The numbers generated in this assay were relative to using BSA as a standard. The plates were read at $A_{560}$. The results of the assay indicate that Anti-FLAG® M2 was incorporated to approximately 3.90 and 4.04 μg/cm² over background for the unblocked and blocked respectively.

Example 11
Preparation of a Poly dT Polymerase Chain Reaction (PCR) Plate

Preparation of Oligo-dT-30 C6-amine-Maleimide Conjugate: To a vial containing 0.5 μmoles of oligo dT-30 C6 amine (9.1 kDa) was added 0.5 mL of deionized water. The solution was then diluted 1:2 with 0.1 M sodium phosphate pH 7.0. To the stirring, cloudy reaction mixture was added 21 μL of a 10 mg/mL solution of maleimidobutyric NHS ester in anhydrous DMF. The reaction was allowed to stir at room temperature for 1.5 hours. A portion of the reaction mixture was removed and diluted to 0.01 μmole/mL in PBS buffer pH 7.0 and supplemented to a final concentration of 0.5 M sodium chloride. Several 5-fold serial dilutions were made to give concentrations of activated oligo dT 10,000, 2,000, 400, 80, and 16 pmoles/mL.

Preparation of a Polypropylene Dextran-SATA 96 well PCR Plate: To a PCR 96 well polypropylene plate was added 50 μL of a 0.15 mg/mL in total dextran solution of dextran-lysine-benzophenone-s-acetylthioglycolic acid in water. The 96 well plate was allowed to dry overnight in an oven at 40° C. with air blowing over it. The dried 96 well plate was then photoirradiated for 32 minutes at approximately 9.0 mWatts/cm$^2$. The 96 well plate was then soaked overnight in 300 μL of 0.025 M sodium acetate. The 96 well plate was then washed 3 times with 300 μL of 0.025 M sodium acetate and twice with 300 μL of water.

Preparation of a Polypropylene Dextran-Oligo-dT 96 well PCR plate: The dextran-SATA 96 well polypropylene PCR plate prepared as described above was loaded with 100 μL of 0.1 M hydroxylamine in 0.1 M sodium phosphate, pH 6.5, and allowed to incubate at room temperature for 15 minutes with orbital mixing. The plate was then washed 3 times with 300 μL of 0.1 M sodium phosphate pH 7.0 and loaded with 50 μL of the various concentration levels of the 9.1 kDa target molecule oligo dT-30 C6-amine-maleimide conjugate, and allowed to incubate at 2–8° C. overnight with rapid orbital mixing. The 96 well plate was then washed 3 times with 200 μL of 0.1 M sodium pH 7.0. 50 μl of a 1.0 mM β-mercaptoethanol solution in 0.1 M sodium phosphate pH 7.0 was added to the wells and allowed to incubate for 15 minutes at room temperature with orbital mixing. The plate was then washed 3 times with 0.1 M sodium phosphate buffer pH 7.0. To each well of the plate was added 300 μL of a 1 mM n-ethylmaleimide solution in 0.1 M sodium phosphate pH 7.0 and allowed to incubate at room temperature for 1 hour with orbital mixing. The plate was then washed 3 times with a 0.1 M sodium phosphate pH 7.0. The oligo dT plates were suitable for capturing mRNA and in turn using them to perform RT-PCR.

Example 12
Preparation of High Capacity Nickel Chelate 96 Well Plates Using High Throughput Technology Preparation of High Capacity Nickel Chelate 96 well plate: Using an Oyster Bay dispenser, which has been first primed by dispensing at least 10-fold the volume needed to fill a single 96 well plate, TCT 96 well plates were filled with 200 μL of a 0.15 mg/mL solution of 50% dextran-lysine-benzophenone-bis (N,N'-carboxymethyl)cysteine and 50% dextran-lysine-bis (N,N'-carboxymethyl)cysteine, both as prepared in example 1. The average molecular weight of the polymers was 1,104 kDa with a range of 300 kDa to 10,000 kDa). A check plate was made every 30 minutes to be sure that the weight of the filled plate was within the specified weight representing 200 μL of solution in each well. The 96 well plates were placed on large drying trays and allowed to dry in a drying closet, in the dark overnight at 40–50° C. The dried 96 well plates were then photoirradiated using a Fusion UV Converyor System with the conveyer belt set at 8 feet/minute with the lamp power at 400 watts/in. A radiometer, IL290 Light Bug, was run through the converyer belt to verify the desired energy in the range of 3,000–4,000 mjoules/cm$^2$. The plates were photoirradiated at about 800 to 960 plates per hour. The 96 well plates were then soaked overnight in 250 μL of water, which was dispensed through the Oyster Bay. Again, using the Oyster Bay, the 96 well plates were then washed twice with 250 μL of water and loaded with 250 μL of a 3-(N-morpholino)butanesulfonic acid (MOPS) saline pH 7.0 with 1 mM nickel sulfate hexahydrate buffer and allowed to soak overnight at room temperature. The 96 well plates were then washed once with 300 μL of 0.05 M acetic acid, once with 300 μL of water, and then twice with 300 μL of MOPS-Hibitane pH 7.0 buffer. The plates were then stacked and allowed to dry at room temperature prior to use.

Protein Binding Capacity: The High Capacity Nickel Chelate 96 well plates, prepared as described above, were tested by determining the total amount of recombinant metal chelating protein, FLAG-BAP, that could be captured per well. A 0.15 mg/mL solution of a FLAG-BAP solution in TBS pH 8.0 was incubated in the wells for 4 hours at room temperature. After incubating 4 hours, the wells were washed 3 times with 300 μL of PBST, followed by 3 times with 300 μL of water. A BCA protein assay was run on a random sampling of wells from four different plates to determine the total amount of protein bound per well. Results of the protein binding capacity were approximately 6 micrograms of protein per well or 4.2 micrograms protein per cm$^2$.

We claim:

1. An assay platform for isolating, harvesting, detecting or quantifying a target polypeptide molecule, the platform comprising a substrate, a polymer matrix attached to the substrate, and a binding ligand attached to the polymer matrix having an affinity for the target polypeptide molecule, the binding ligand being selected from the group consisting of metal chelates, anion exchangers, cation exchangers, hydrophobic binding ligands, antibodies, streptavidin, avidin, biotin, glutathione, protein A, protein G, and protein L, wherein the polymer matrix is covalently attached directly to the substrate to provide a density of the polymer matrix on the substrate of at least 2 μg/cm$^2$, and the density of the binding ligand attached to the polymer matrix is at least 1 nanomole/cm$^2$.

2. The assay platform according to claim 1 wherein the density of the polymer matrix on the substrate is 4 μg/cm$^2$ to 30 μg/cm$^2$.

3. The assay platform according to claim 1 wherein the density of the polymer matrix on the substrate is 6 μg/cm$^2$ to 15 μg/cm$^2$.

4. The assay platform according to claim 1 wherein the density of the binding ligand attached to the polymer matrix is 1.2 nanomoles/cm$^2$ to 185 nanomoles cm$^2$.

5. The assay platform according to claim 1 wherein the density of the binding ligand attached to the polymer matrix is 1.5 nanomoles/cm$^2$ to 90 nanomoles cm$^2$.

6. The assay platform according to claim 1 wherein the density of the binding ligand attached to the polymer matrix is 1.8 nanomoles/cm$^2$ to 15 nanomoles/cm$^2$.

7. The assay platform according to claim 1 wherein the substrate is a multi-well plate.

8. The assay platform according to claim 7 wherein the multi-well plate is a 96, 384 or 1536 well polystyrene or polypropylene multiwell plate.

9. The assay platform according to claim 1 wherein the substrate is glass.

10. The assay platform according to claim 1 wherein the substrate is plastic.

11. The assay platform according to claim 1 wherein the assay platform has the capacity to bind polypeptides having a molecular weight of 3.5 kDa to 500 kDa in an amount of 0.5 μg/cm$^2$ to 20 μg/cm$^2$.

12. The assay platform according to claim 1 wherein the assay platform has the capacity to bind polypeptides having a molecular weight of 10 kDa to 500 kDa in an amount of 1 μg/cm$^2$ to 20 μg/cm$^2$.

13. The assay platform according to claim 1 wherein the assay platform has the capacity to bind polmypeptides having a molecular weight of 10 kDa to 350 kDa in an amount of 2 μg/cm$^2$ to 20 μg/cm$^2$.

14. The assay platform according to claim 1 wherein the assay platform has the capacity to bind polypeptides having a molecular weight of 10 kDa to 350 kDa in an amount of 3 μg/cm$^2$ to 15 μg/cm$^2$.

15. The assay platform according to claim 1 wherein the assay platform has the capacity to bind polypeptides having a molecular weight of 10 kDa to 350 kDa in an amount of 4 $\mu$g/cm$^2$ to 10 $\mu$g/cm$^2$.

16. The assay platform according to claim 1 wherein the polymer matrix binds to polypeptide target molecules having a molecular weight up to 350 kDa in an amount of at least 2 $\mu$g/cm$^2$.

17. The assay platform according to claim 1 wherein the binding ligand comprises a metal chelate.

18. The assay platform according to claim 17 wherein the metal chelate is a metal chelate derived from iminodiacetic acid, nitriloacetic acid or an analog thereof.

19. The assay platform according to claim 1 wherein the binding ligand is covalently attached to the polymer molecule through a spacer.

20. The assay platform according to claim 19 wherein the spacer comprises a lysine derivative.

21. The assay platform according to claim 19 wherein the spacer further comprises an aminocaproic acid derivative.

22. The assay platform according to claim 1 wherein the substrate is a multiwell polystyrene plate, wherein the polymer matrix comprises a dextran polymer or derivative thereof, wherein the binding ligand is a nickel chelate, and wherein the polymer matrix has a binding ligand density of 1.5 nanomoles/cm$^2$ to 7.5 nanomoles/cm$^2$.

23. The assay platform according to claim 1 wherein the substrate is a multiwell polystyrene plate, wherein the polymer matrix comprises a dextran polymer or derivative thereof, wherein the binding ligand is a Gallium or Iron chelate, and wherein the polymer matrix has a binding ligand density of 1.5 nanomoles/cm$^2$ to 7.5 nanomoles/cm$^2$.

24. The assay platform according to claim 1 wherein the substrate is a multiwell polystyrene plate, wherein the polymer matrix comprises a dextran polymer or derivative thereof, wherein the binding ligand is glutathione, and wherein the polymer matrix has a binding ligand density of 1.5 nanomoles/cm$^2$ to 7.5 nanomoles/cm$^2$.

25. The assay platform according to claim 1 wherein the substrate is a multiwell polystyrene plate or a multiwell polypropylene plate, wherein the polymer matrix comprises a dextran polymer or derivative thereof, wherein the binding ligand is streptavidin, and wherein the polymer matrix has a binding ligand density of 1.5 $\mu$g/cm$^2$ to 7.5 $\mu$g/cm$^2$.

26. The assay platform according to claim 1 wherein the substrate is a multiwell polystyrene plate, wherein the polymer matrix comprises a dextran polymer or derivative thereof, wherein the binding ligand is selected from the group consisting of protein A, protein G, protein L, or a mixture thereof and wherein the polymer matrix has a binding ligand density of 1.5 $\mu$g/cm$^2$ to 7.5 $\mu$g/cm$^2$.

27. An assay platform according to claim 1 wherein the polymer matrix is a crosslinked mixture of at least two polymers, the crosslinked matrix being formed by (i) combining the substrate with a mixture comprising first and second polymers, the first polymer possessing a reactive group which upon activation crosslinks the first and second polymers to form the polymer matrix and covalently attaches the polymer matrix to the substrate, the second polymer having an absence of such reactive groups, and (ii) activating the reactive groups of the first polymer in the combination to form the polymer matrix and covalently bind the matrix to the substrate, wherein the density of the crosslinked polymer matrix on the substrate is at least 2 $\mu$g/cm$^2$.

28. The assay platform according to claim 27 wherein the polymer matrix comprises a natural polymer.

29. The assay platform according to claim 27 wherein the polymer matrix comprises a dextran polymer or derivative thereof.

30. The assay platform according to claim 27 wherein the polymer matrix comprises a synthetic polymer.

31. The assay platform according to claim 27 wherein the assay platform has the capacity to bind polypeptides having a molecular weight of less than 3.5 kDa in an amount of at least 1 nanomole/cm$^2$.

32. The assay platform of claim 1 wherein the substrate is a multiwell plate and the polymer matrix comprises a polysaccharides or a derivatized polysaccharide.

33. The assay platform of claim 1 wherein the substrate is a multiwell plate, the polymer matrix comprises a polysaccharide or a derivatized polysaccharide, and the binding ligand comprises a metal chelate.

34. The assay platform of claim 1 wherein the substrate is a multiwell plate, the polymer matrix comprises a polysaccharide or a derivatized polysaccharide, and the binding ligand comprises a metal chelate of iminodiacetic acid, nitrilotriacetic acid or an analog thereof.

35. The assay platform of claim 1 wherein binding ligand is selected from the group consisting of metal chelates, anion exchangers, cation exchangers, hydrophobic binding ligands, antibodies, and streptavidin.

36. The assay platform of claim 35 wherein the polymer matrix comprises a natural polymer derivative.

37. The assay platform of claim 35 wherein the polymer matrix comprises a polysaccharide derivative.

38. The assay platform of claim 35 wherein the polymer matrix comprises a dextran derivative.

39. The assay platform of claim 35 wherein the polymer matrix comprises a natural polymer derivative and the substrate is a multiwell plate.

40. The assay platform of claim 35 wherein the polymer matrix comprises a polysaccharide derivative and the substrate is a multiwell plate.

41. The assay platform of claim 35 wherein the polymer matrix comprises a dextran derivative and the substrate is a multiwell plate.

42. The assay platform of claim 35 wherein the polymer matrix comprises a dextran derivative, the substrate is a multiwell plate, the binding ligand is a metal chelate and the metal chelate comprises copper.

43. The assay platform of claim 1 wherein binding ligand is a metal chelate and the polymer matrix comprises a polysaccharide derivative.

44. The assay platform of claim 1 wherein binding ligand is a metal chelate and the polymer matrix comprises a dextran derivative.

45. The assay platform of claim 1 wherein binding ligand is biotin, avidin or streptavidin and the polymer matrix comprises a natural polymer derivative.

46. The assay platform of claim 1 wherein binding ligand is biotin, avidin or streptavidin and the polymer matrix comprises a polysaccharide derivative.

47. The assay platform of claim 1 wherein binding ligand is biotin, avid in or streptavidin and the polymer matrix comprises a dextran derivative.

48. The assay platform of claim 1 wherein binding ligand is an antibody and the polymer matrix comprises a natural polymer derivative.

49. The assay platform of claim 1 wherein binding ligand is an antibody and the polymer matrix comprises a polysaccharide derivative.

50. The assay platform of claim 1 wherein binding ligand is an antibody and the polymer matrix comprises a dextran derivative.

51. The assay platform of claim 1 wherein binding ligand is glutathione and the polymer matrix comprises a natural polymer derivative.

52. The assay platform of claim 1 wherein binding ligand is glutathione and the polymer matrix comprises a polysaccharide derivative.

53. The assay platform of claim 1 wherein binding ligand is glutathione and the polymer matrix comprises a dextran derivative.

54. The assay platform of claim 1 wherein binding ligand is an anion exchanger and the polymer matrix comprises a natural polymer derivative.

55. The assay platform of claim 1 wherein binding ligand is an anion exchanger and the polymer matrix comprises a polysaccharide derivative.

56. The assay platform of claim 1 wherein binding ligand is an anion exchanger and the polymer matrix comprises a dextran derivative.

57. The assay platform of claim 1 wherein binding ligand is a cation exchanger and the polymer matrix comprises a polysaccharide derivative.

58. The assay platform of claim 1 wherein binding ligand is a cation exchanger and the polymer matrix comprises a dextran derivative.

59. The assay platform of claim 1 wherein binding ligand is an antibody, the polymer matrix comprises a dextran derivative, and the substrate is multiwell plate.

60. The assay platform according to claim 1 wherein the substrate is a Matrix Assisted Laser Desorption Ionization (MALDI) plate.

* * * * *

UNITED STATES PATENT AND TRADEMARK OFFICE
CERTIFICATE OF CORRECTION

PATENT NO.   : 6,825,032 B2
DATED        : November 30, 2004
INVENTOR(S)  : John Dapron et al.

It is certified that error appears in the above-identified patent and that said Letters Patent is hereby corrected as shown below:

<u>Column 32,</u>
Line 61, "polmypeptides" should read -- polypeptides --.

Signed and Sealed this

Nineteenth Day of April, 2005

JON W. DUDAS
*Director of the United States Patent and Trademark Office*